US009125759B2

(12) United States Patent
Greenhalgh et al.

(10) Patent No.: US 9,125,759 B2
(45) Date of Patent: Sep. 8, 2015

(54) BIOCOMPOSITE MEDICAL CONSTRUCTS INCLUDING ARTIFICIAL TISSUES, VESSELS AND PATCHES

(71) Applicant: MiMedx Group, Inc., Kennesaw, GA (US)

(72) Inventors: Kerriann Greenhalgh, Tampa, FL (US); Mengyan Li, Tampa, FL (US); Thomas J. Koob, Kennesaw, GA (US)

(73) Assignee: MiMedx Group, Inc., Marietta, GA (US)

( * ) Notice: Subject to any disclaimer, the term of this patent is extended or adjusted under 35 U.S.C. 154(b) by 0 days.

(21) Appl. No.: 13/729,668

(22) Filed: Dec. 28, 2012

(65) Prior Publication Data
US 2013/0131781 A1     May 23, 2013

Related U.S. Application Data

(62) Division of application No. 12/576,423, filed on Oct. 9, 2009, now Pat. No. 8,367,148.

(60) Provisional application No. 61/103,995, filed on Oct. 9, 2008, provisional application No. 61/138,165, filed on Dec. 17, 2008.

(51) Int. Cl.
*A61F 2/06*     (2013.01)
*A61F 2/82*     (2013.01)
(Continued)

(52) U.S. Cl.
CPC ............. *A61F 2/82* (2013.01); *A61B 19/026* (2013.01); *A61F 2/06* (2013.01); *A61L 15/325* (2013.01);
(Continued)

(58) Field of Classification Search
CPC ............... A61F 2/04; A61F 2/06; A61F 2/82; A61L 15/325; A61L 27/24
USPC .................... 623/1.47, 1.54, 23.71
See application file for complete search history.

(56) References Cited

U.S. PATENT DOCUMENTS 3,316,699 A    5/1967   Mattingly
3,700,489 A    10/1972   Borysko
(Continued)

FOREIGN PATENT DOCUMENTS

CA           2285161       4/2001
EP            1319415       6/2003
(Continued)

OTHER PUBLICATIONS

Brunelli et al., Slip-knot flexor tendon suture in zone II allowing immediate mobilisation, The Hand, 1983, vol. 15, pp. 352-358.
(Continued)

*Primary Examiner* — Randy Shay
*Assistant Examiner* — Dinah Baria
(74) *Attorney, Agent, or Firm* — Myers Bigel Sibley & Sajovec, P.A.

(57) ABSTRACT

The disclosure describes methods of making collagen based biocomposite constructs and related devices. The methods include: (a) winding at least one collagen fiber a number of revolutions about a length of a support member having a long axis, the winding having at least one defined pitch and/or fiber angle relative to the long axis of the support member to form an elongate construct; and (b) applying a fluid polymeric material, such as, for example, an acrylate emulsion and/or other thermoplastic material, onto the collagen fiber during the winding step. Optionally, the fluid polymeric material can include antibiotics and/or other therapeutic agents for additional function/utility.

32 Claims, 26 Drawing Sheets

(51) Int. Cl.
| | |
|---|---|
| *A61B 19/02* | (2006.01) |
| *A61L 15/32* | (2006.01) |
| *A61L 27/24* | (2006.01) |
| *A61L 27/58* | (2006.01) |
| *A61B 17/04* | (2006.01) |
| *A61B 17/06* | (2006.01) |
| *A61B 17/11* | (2006.01) |
| *B29C 53/58* | (2006.01) |
| *B29C 53/66* | (2006.01) |

(52) U.S. Cl.
CPC ............... *A61L 27/24* (2013.01); *A61L 27/58* (2013.01); *A61B 17/0401* (2013.01); *A61B 17/06166* (2013.01); *A61B 17/1128* (2013.01); *A61B 17/1146* (2013.01); *A61B 2019/0267* (2013.01); *B29C 53/58* (2013.01); *B29C 53/66* (2013.01)

(56) References Cited

U.S. PATENT DOCUMENTS

| | | | |
|---|---|---|---|
| 4,590,928 | A | 5/1986 | Hunt et al. |
| 4,778,467 | A | 10/1988 | Stensaas et al. |
| 4,792,336 | A | 12/1988 | Hlavacek et al. |
| 4,841,962 | A | 6/1989 | Berg et al. |
| 4,883,486 | A | 11/1989 | Kapadia et al. |
| 4,923,380 | A | 5/1990 | Huc et al. |
| 4,979,956 | A | 12/1990 | Silvestrini |
| 5,028,695 | A | 7/1991 | Eckmayer et al. |
| 5,078,744 | A | 1/1992 | Chvapil |
| 5,106,949 | A | 4/1992 | Kemp et al. |
| 5,162,430 | A | 11/1992 | Rhee et al. |
| 5,256,418 | A | 10/1993 | Kemp et al. |
| 5,263,984 | A | 11/1993 | Li et al. |
| 5,378,469 | A | 1/1995 | Kemp et al. |
| 5,569,302 | A | 10/1996 | Proto et al. |
| 5,656,605 | A | 8/1997 | Hansson et al. |
| 5,713,374 | A | 2/1998 | Pachence et al. |
| 5,718,012 | A | 2/1998 | Cavallaro |
| 5,718,717 | A | 2/1998 | Bonutti |
| 6,090,117 | A | 7/2000 | Shimizu |
| 6,224,630 | B1 | 5/2001 | Bao et al. |
| 6,277,397 | B1 | 8/2001 | Shimizu |
| 6,280,474 | B1 | 8/2001 | Cassidy et al. |
| 6,292,697 | B1 | 9/2001 | Roberts |
| 6,335,007 | B1 | 1/2002 | Shimizu et al. |
| 6,420,625 | B1 * | 7/2002 | Jones et al. ............ 604/367 |
| 6,514,286 | B1 * | 2/2003 | Leatherbury et al. ...... 623/11.11 |
| 6,531,147 | B2 | 3/2003 | Sawhney et al. |
| 6,565,960 | B2 | 5/2003 | Koob et al. |
| 6,589,257 | B1 | 7/2003 | Shimizu |
| 6,592,623 | B1 | 7/2003 | Bowlin et al. |
| 6,596,296 | B1 | 7/2003 | Nelson et al. |
| 6,645,247 | B2 | 11/2003 | Ferree |
| 6,692,528 | B2 | 2/2004 | Ward et al. |
| 6,713,537 | B1 | 3/2004 | Ueda et al. |
| 6,730,124 | B2 | 5/2004 | Steiner |
| 6,752,831 | B2 | 6/2004 | Sybert et al. |
| 6,821,530 | B2 | 11/2004 | Koob et al. |
| 6,866,681 | B2 | 3/2005 | Laboureau et al. |
| 6,936,072 | B2 | 8/2005 | Lambrecht et al. |
| 6,953,482 | B2 | 10/2005 | Doi et al. |
| 6,955,683 | B2 | 10/2005 | Bonutti |
| 6,977,231 | B1 | 12/2005 | Matsuda |
| 7,048,963 | B2 | 5/2006 | Braithwite et al. |
| 7,084,082 | B1 | 8/2006 | Shimizu |
| 7,090,690 | B2 | 8/2006 | Foerster et al. |
| 7,105,021 | B2 | 9/2006 | Edens et al. |
| 7,115,146 | B2 | 10/2006 | Boyer et al. |
| 7,135,040 | B2 | 11/2006 | Wang et al. |
| 7,264,859 | B2 * | 9/2007 | Rouns et al. ............ 428/36.91 |
| 7,309,359 | B2 | 12/2007 | Trieu et al. |
| 7,354,627 | B2 | 4/2008 | Pedrozo et al. |
| 7,615,063 | B2 | 11/2009 | Doi et al. |
| 7,650,742 | B2 | 1/2010 | Ushijima |
| 2001/0018619 | A1 | 8/2001 | Enzerink et al. |
| 2002/0037940 | A1 | 3/2002 | Koob et al. |
| 2002/0123805 | A1 | 9/2002 | Murray et al. |
| 2003/0003157 | A1 | 1/2003 | Ohan et al. |
| 2003/0100108 | A1 | 5/2003 | Altman et al. |
| 2003/0211130 | A1 * | 11/2003 | Sanders et al. ........... 424/423 |
| 2003/0230316 | A1 | 12/2003 | Glucksman et al. |
| 2004/0110439 | A1 | 6/2004 | Chaikof et al. |
| 2004/0131562 | A1 | 7/2004 | Gower et al. |
| 2004/0193241 | A1 | 9/2004 | Stinson |
| 2004/0224406 | A1 | 11/2004 | Altman et al. |
| 2004/0267362 | A1 | 12/2004 | Hwang et al. |
| 2005/0009178 | A1 | 1/2005 | Yost et al. |
| 2006/0095134 | A1 | 5/2006 | Trieu et al. |
| 2006/0200250 | A1 * | 9/2006 | Ku ............................ 623/23.71 |
| 2006/0257377 | A1 | 11/2006 | Atala et al. |
| 2006/0263417 | A1 | 11/2006 | Lelkes et al. |
| 2007/0038290 | A1 * | 2/2007 | Huang et al. ............. 623/1.16 |
| 2007/0118217 | A1 | 5/2007 | Brulez et al. |
| 2007/0248643 | A1 | 10/2007 | Devore et al. |
| 2007/0269481 | A1 | 11/2007 | Li et al. |
| 2008/0020012 | A1 | 1/2008 | Ju et al. |
| 2008/0038352 | A1 | 2/2008 | Simpson et al. |
| 2008/0124371 | A1 | 5/2008 | Turos et al. |
| 2008/0161917 | A1 | 7/2008 | Koob et al. |
| 2008/0188933 | A1 | 8/2008 | Koob et al. |
| 2008/0199506 | A1 | 8/2008 | Horres et al. |
| 2008/0200992 | A1 | 8/2008 | Koob et al. |
| 2008/0215150 | A1 | 9/2008 | Koob et al. |
| 2008/0286332 | A1 * | 11/2008 | Pacetti ........................ 424/424 |
| 2008/0300683 | A1 | 12/2008 | Altman et al. |
| 2009/0216233 | A1 | 8/2009 | Wiedrich et al. |
| 2009/0287308 | A1 | 11/2009 | Davis et al. |
| 2010/0076462 | A1 | 3/2010 | Bakos et al. |
| 2010/0094318 | A1 | 4/2010 | Li et al. |

FOREIGN PATENT DOCUMENTS

| | | |
|---|---|---|
| EP | 1493404 | 1/2005 |
| WO | WO 82-01647 | 5/1982 |
| WO | WO 96-14095 | 5/1996 |
| WO | WO 01/15754 | 3/2001 |
| WO | WO 01-72241 | 10/2001 |
| WO | WO 2008-041183 | 4/2008 |
| WO | WO 2008/093342 * | 7/2008 |

OTHER PUBLICATIONS

Greis et al, The influence of tendon length and fit on the strength of the tendon-bone tunnel complex, Am. J. Sports Med., 2001, 29:493-497.
Becker et al., Early active motion following a beveled technique of flexor tendon repair: Report on fifty cases, Journal of Hand Surgery, 1979, vol. 4 No. 5, pp. 454-460.
Grog, The Reef (Square) Knot, Animated Knots by Grog, downloaded at http://www.animatedknots.com/reef/index.php, on May 28, 2009 using WayBack Machine on www.archive.org for publication date of Dec. 26, 2005.
International Search Report and Written Opinion for related PCT application No. PCT/US2009/005540, Date of mailing May 26, 2010.
Koob et al., Biomimetic approaches to tendon repair, Comp. Biochem. Physiol. A Mol. Integr. Phys., 2002, 133: 1171-1192.
Koob et al., Material properties of NDGA-collagen composite fibers: development of biologically based tendon constructs, Biomaterials, 2002, 23:202-212.
Koob et al., Mechanical and thermal properties of novel polymerized NDGA-gelatin hydrogels, Biomaterials, 2002, 24:1285-1292.
Koob et al., Biocompatibility of NDGA-polymerized collagen fibers. I. Evaluation of cytotoxicity with tendon fibroblasts in vitro, © 2001 John Wiley & Sons, Inc.
Koob et al., Biocompatibility of NDGA-polymerized collagen fibers. II. Attachment, proliferation, and migration of tendon fibroblasts in vitro, © 2001 John Wiley & Sons, Inc.
Martin et al., Anterior Cruciate Ligament Graft Preparation: A New and Quick Alternative to the Whipstitch, Arthroscopy: The Journal of Arthroscopic & Related Surgery, Online Publication Date of Nov. 29, 2006.

(56) References Cited

OTHER PUBLICATIONS

Messina, The double armed suture: Tendon repair with immediate mobilization of the fingers, Journal of Hand Surgery, 1992, 17A:137-142.
Nottage et al., Arthoscopic Knot Tying Techniques, Arthroscopy: The Journal of Arthroscopic & Related Surgery 15(1999): 515-521.
Powell et al., Forces transmitted along human flexor tendons during passive and active movements of the fingers, J. Hand Surg., 2004, 29:4:386-389.
Rodeo et al., Tendon healing in a bone tunnel. A biomechanical and histological study in a dog, J. Bone Joint Surg., 1993, 75:1795-1803.
Savage et al., Flexor tendon repair using a "six strand" method of repair and early active mobilisation, Journal of Hand Surgery, (British Volume,1989), 14B:396-399.
Silva et al., The insertion site of the canine flexor digitorum profundus tendon heals slowly following injury and suture repair, J. Orthop. Res., 2002, 20:447-453.
Trotter et al., Molecular structure and functional morphology of echinoderm collagen fibrils, Cell Tiss. Res., 1994, 275: 451-458.
Werner et al., Neutral Red Assay of the Cytotoxicity of Fluorocarbon-Coated Polymethylmethacrylate Intraocular Lenses In Vitro, Journal of Biomedical Materials Research, Nov. 9, 1999, pp. 814-819, vol. 48, No. 6.
Product advertisement, Conair QB3ECS Quick Braid Styling Kit, © 2007 (1 page).
Integra™ NeuraGen™ Nerve Guide, Product Brochure, 4 pages 2005.
Integra™ NeuraGen™ Nerve Guide, Product Webpage, http://www.integra-ls.com/products/?product=88, Date unknown but believed to be prior to the filing date of the present application, 2 pages.
Integra™ NeuraWrap™ Nerve Protector, Product Webpage, http://www.integra-ls.com/products/?product=198, Date unknown but believed to be prior to the filing date of the present application, 2 pages.
Kakisis, J., et al., Artificial blood vessel: The Holy Grail of peripheral vascular surgery, Journal of Vascular Surgery, vol. 41, Issue 2, 2003, pp. 349-354 (abstract only).
Biosingularity, Advances in biological systems, Google Ad, MIT Technology Review, 2006, 1 Page.

* cited by examiner

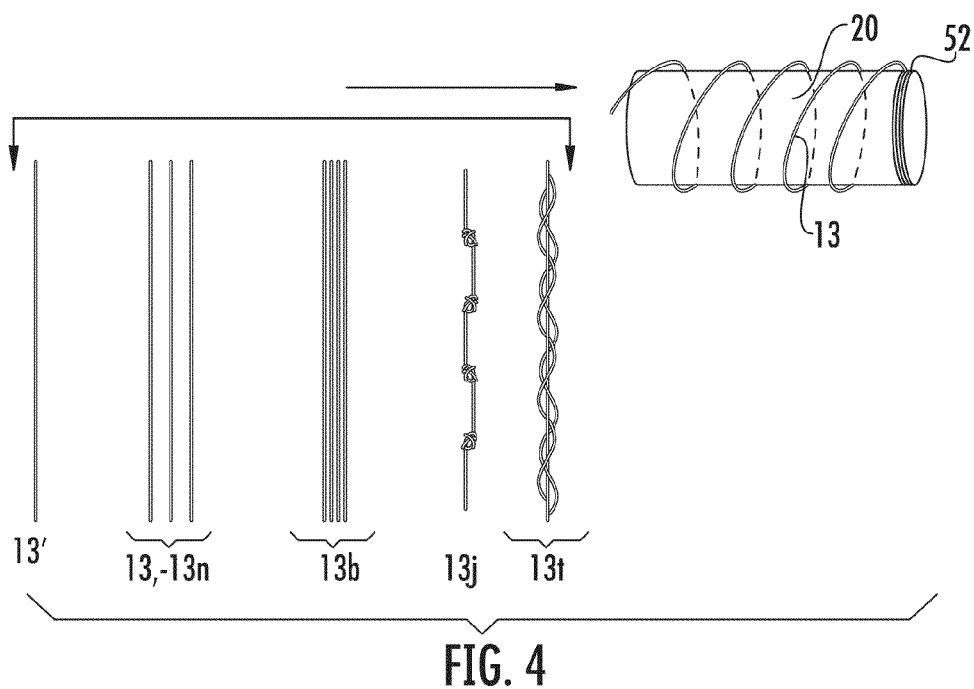
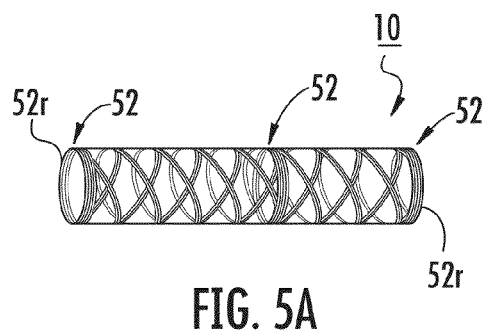
FIG. 5A
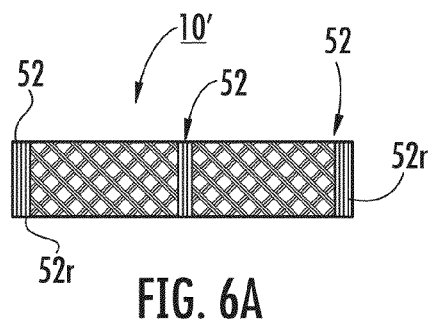
FIG. 6A
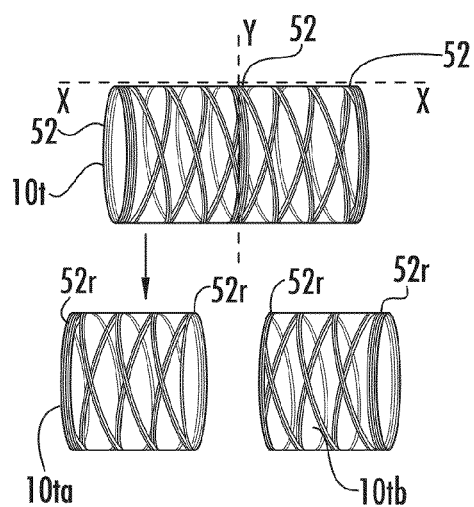
FIG. 5B
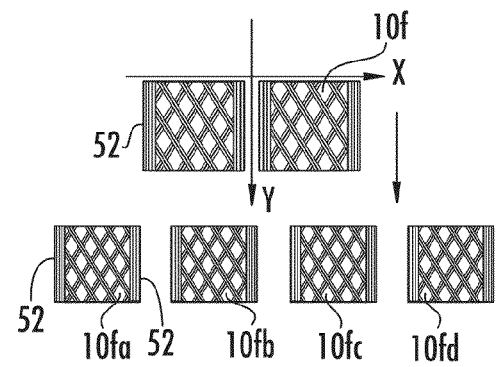
FIG. 6B THE WINDING CAN BE CARRIED OUT SO THAT THE AT LEAST ONE FIBER TURNS ABOUT THE SUPPORT MEMBER IN ONE OF A CLOCKWISE OR COUNTERCLOCKWISE DIRECTION ALONG A FIRST LENGTHWISE DIRECTION FOR A FIRST LAYER, THEN REVERSES TO TRAVEL IN AN OPPOSING LENGTHWISE DIRECTION AND CONTINUES TO TURN ABOUT THE SUPPORT MEMBER IN THE SAME CLOCKWISE OR COUNTERCLOCKWISE DIRECTION TO FORM A SECOND OVERLYING ADJACENT LAYER.
180

FIG. 11

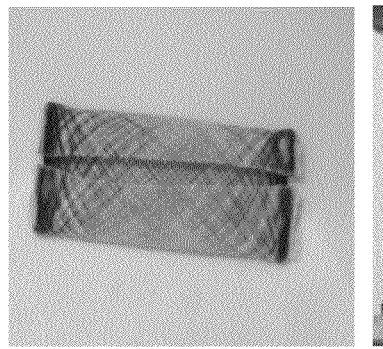 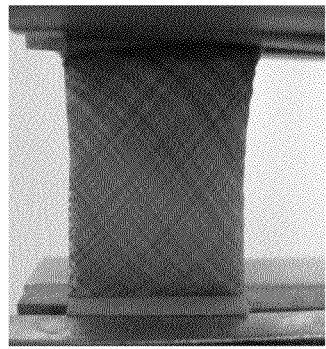 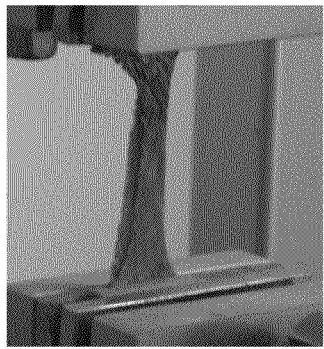
CUT AND HYDRATING — FIG. 14A
RELAXED FIBER STATE — FIG. 14B
FIBERS ALIGN TO RELAXED STATE — FIG. 14C
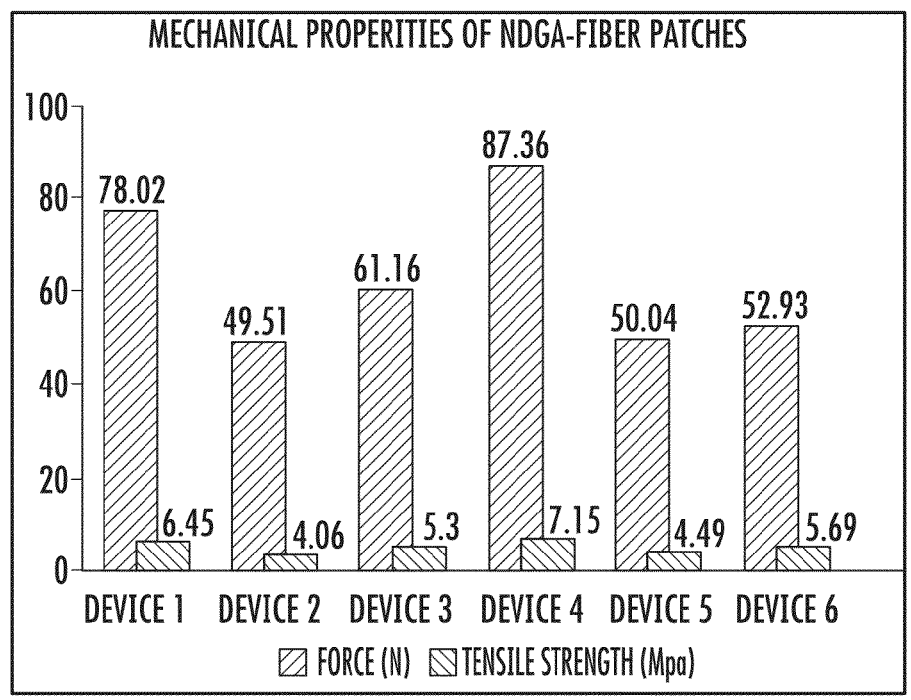
FIG. 15

BIOCOMPOSITE MEDICAL CONSTRUCTS INCLUDING ARTIFICIAL TISSUES, VESSELS AND PATCHES

RELATED APPLICATIONS

This application is a divisional application of U.S. patent application Ser. No. 12/576,423, filed Oct. 9, 2009, which claims the benefit of and priority to U.S. Provisional Application Ser. No. 61/103,995 filed Oct. 9, 2008, and U.S. Provisional Application Ser. No. 61/138,165 filed Dec. 17, 2008, the contents of which are hereby incorporated by reference as if recited in full herein.

FIELD OF THE INVENTION

The invention relates to biomedical materials and products.

BACKGROUND OF THE INVENTION

Koob et al. have described methods of producing nordihydroguaiaretic acid (NDGA) polymerized collagen fibers for various biomedical applications, some with tensile strengths similar to that of natural tendon (e.g., about 91 MPa). See, for example, Koob and Hernandez, *Material properties of polymerized NDGA-collagen composite fibers: development of biologically based tendon constructs*, Biomaterials 2002 January; 23 (1): 203-12; and U.S. Pat. No. 6,565,960, the contents of which are hereby incorporated by reference as if recited in full herein.

SUMMARY OF EMBODIMENTS OF THE INVENTION

Embodiments of the present invention are directed to methods and systems for making biomaterials and/or collagen constructs for medical use and related biomaterials and/or medical constructs.

Embodiments of the present invention are directed to methods of fabricating a medical construct. The methods include: (a) winding at least one collagen fiber a number of revolutions about a length of a support member having a long axis to form the construct, the winding having at least one defined pitch and/or fiber angle relative to the long axis of the support member; and (b) applying a non-cytotoxic polymeric material (such as an acrylate emulsion) onto the at least one collagen fiber during the winding step.

The at least one collagen fiber can be provided as a spooled supply of the at least one collagen fiber. The length of the fiber(s) can be any appropriate length and may be, on average between about 1 m to about 100 m for the winding step. Optionally, the liquid polymeric material can include antibiotics and/or biologically active agents for additional function/utility.

The winding step may be carried out so that the at least one collagen fiber defines a fiber mesh pattern with interstitial spaces and the applying step can be carried out so that the polymeric material, e.g., the acrylate, enters the interstitial spaces and forms a continuous solid film. The film may be permeable to small ions or low molecular weight (<150 g/mol) compounds, flexible and optically transmissive, e.g., translucent or transparent, or may be opaque. Optionally, any heat source can be used to aid in the polymeric (e.g., polyacrylate) application.

The method may optionally include spin-coating the elongate construct with a liquid polymer (such as, for example, an acrylate emulsion) after the winding step, then incubating the spin-coated construct at a defined temperature for a defined time to form a dry polymeric coating (e.g., film) on the elongate construct. The spin-coating and incubation steps may be repeated at least once. Any heat source can be used to aid in the polyacrylate application and/or drying.

The at least one collagen fiber can have a diameter (dry) of between 0.05 mm to about 0.2 mm (average) and a length between about 1 m to about 100 m (average). The at least one fiber can be formed with multiple fibers joined end-to-end to form the desired length or can be a single fiber of a continuous length to form the desired length for the winding.

Other embodiments are directed to medical devices. The devices include an elastic tube with a wall surrounding an axially extending cavity. The wall has at least one collagen fiber of a length (e.g., typically between about 1 m to about 100 m) arranged in a fiber mesh pattern of intersecting segments over at least a major length of the tube and a polymeric film that embeds or encases the at least one collagen fiber and extends over interstitial spaces defined by the fiber mesh pattern.

The medical device can be an artificial vessel and the at least one collagen fiber can be derived from extruded soluble dermal collagen and has a length that is between about 1 m to about 100 m. The at least one collagen fiber can be wound at an angle of between about 1° to 90° relative to a first plane normal to a longitudinal axis of the tube and the tube can include multiple overlying layers of the at least one collagen fiber.

The medical device can be a patch and the at least one fiber may have a diameter when dry of between about 0.05 mm to about 0.2 mm (average). The at least one collagen fiber can be wound about a longitudinal axis of the tube at an angle of between about 5° to 55° relative to the first plane normal to the longitudinal axis. The at least one collagen fiber may optionally be a single collagen fiber in multiple stacked layers.

The medical devices can be artificial tissues, vessels (e.g., aortic stents to vein or artery replacements or repairs), nerve guides or other implantable devices.

Other embodiments are directed to medical patches having at least one collagen fiber, typically with a length of between about 1 m to about 100 m. The at least one collagen fiber can be arranged in a mesh pattern with a plurality of overlying layers defining interstitial spaces. The patches may also include a polymeric film with the fiber(s) embedded therein that extends over the interstitial spaces. The patches may be particularly suitable for dermal and/or epidermal contusions, regions, repairs or disorders or other use.

The patches can include a greater density of the at least one fiber on end portions thereof. The patches can be wound at various angles, typically so that the fibers are arranged at one or more fiber angles between about 1-35 degrees.

Some embodiments are directed to artificial tissues such as vessels. The vessels include a tube with a wall surrounding an axially extending cavity and at least one wound collagen fiber arranged with a number of revolutions over at least a major length of the tube on at least one layer. The tube also includes a polymeric material and the fiber(s) are embedded in the polymeric material. Additional coating layers of polymeric material can be added to seal the fiber(s). One or a plurality of vessels can be formed on a rod having the desired tubular shape.

The vessel tube can be elastic with sufficient rigidity to be able to elastically deform in order to comply with expansion and contraction of blood flow and/or pressure (e.g., able to mimic the natural environment of pulsatile flow) for vascular grafts. The collagen fiber(s) are embedded in the polymeric material. The polymeric material can be configured to only allow small molecular weight ions to penetrate the vessel.

The methods may be carried out using different formulations of the emulsion, including, for example, copolymer emulsions having: (a) about a 4:1 ratio of ethyl acrylate to methyl methacrylate; (b) about a 8:2 ratio of butyl acrylate to styrene; (c) about a 7:3 ratio of butyl acrylate to styrene; (d) about a 8:2 ratio of butyl acryl to methyl methacrylate; or (e) about a 7:3 ratio of butyl acryl to methyl methacrylate.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

BRIEF DESCRIPTION OF THE DRAWINGS

FIG. 4 is a schematic illustration of different collagen fiber configurations that may be used for winding a construct according to embodiments of the present invention.

FIG. 5A is a schematic illustration of a tubular construct with segments having increased fiber density according to embodiments of the present invention.

FIG. 5B is a schematic illustration showing that the tubular structure of FIG. 5A can be separated or cut into multiple different components (shown as two) according to embodiments of the present invention.

FIG. 6A is a schematic illustration of a substantially planar construct with segments having increased fiber density according to embodiments of the present invention.

FIG. 6B is a schematic illustration of the construct shown in FIG. 6A illustrating that the construct can be separated into multiple components (shown as four) according to embodiments of the present invention.

FIG. 11 is a flow chart of an optional method step that may be used to form constructs according to embodiments of the present invention.

FIG. 14A illustrates a prototype construct that was cut and hydrated prior to evaluation.

FIG. 14B illustrates the prototype shown in FIG. 14A mounted in a load cell and with the fibers in a relaxed fiber state.

FIG. 14C illustrates that the fibers of the construct shown in FIGS. 14A and 14B align to a relaxed state after application of a uniaxial load.

FIG. 15 is a bar graph of force (N) and tensile strength (MPa) for six different prototype collagen fiber prototypes according to embodiments of the present invention.

DETAILED DESCRIPTION

Figure 1A:
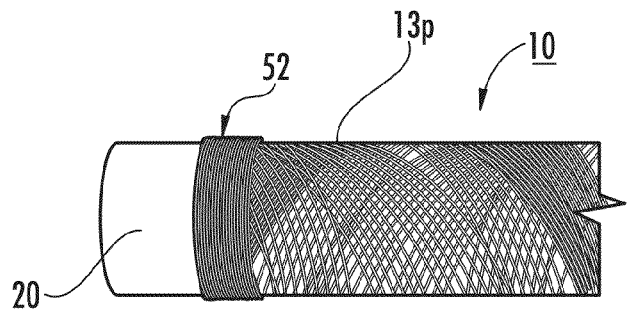
FIG. 1A is a digital photograph of an exemplary collagen fiber construct on an exemplary support member according to embodiments of the present invention.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

The term "implantable" and derivatives thereof means the device can be inserted, embedded, grafted or otherwise acutely or chronically attached or placed in or on a patient. The term "construct" refers to a device and/or material in a final form for use or in a pre-final form. The term "pitch" means winding the fiber at an angle relative to a first plane normal to the longitudinal axis of a core or cavity and/or a wound fiber that is at an angle relative to a first plane normal to the longitudinal axis of a core or cavity. The term "incubate" and derivatives thereof means to heat the device for a desired time to dry the material and/or cause the material to solidify for facilitating cross-linking. The word "embedded" and derivatives thereof mean that the at least one collagen fiber is held in a polymeric matrix and/or encased by the polymeric material (e.g., polymeric film).

The term "patch" refers to a piece or segment of biomaterial that can be placed on and/or affixed to target anatomical structure, typically soft tissue, to treat, protect, repair and/or reinforce a target site. The patch can be any geometric shape but is typically substantially planar and may, in position, conform to the shape of underlying or overlying tissue.

The terms "winding" and "wound" and derivatives thereof mean to wrap about an object or center at least once, typically repeatedly in a defined direction or directions, e.g., to turn in a series of circular motions. In some embodiments, at least one collagen fiber (e.g., a single fiber, multiple fibers, or one or more fiber bundles) turns or rotates its circumferential position about a centerline or long axis. The winding may define a coil (e.g., a series of connected typically substantially concentric rings or spirals), woven and/or braided fiber arrangement with a number of revolutions or turns about a core and/or tube, typically in a regular pattern (but an irregular pattern may also be used) about a length of at least one layer of a tube or cylindrical shape.

Embodiments of the present invention comprise collagen, typically dermal collagen. However, the collagen can be of any form and from any origin. The collagen can be any of the identified collagen genotypes, for example, the interstitial fiber forming collagen types I, II and III, as well as any other substantially fiber forming types of collagen, for example collagen VI. The collagen can be acid soluble collagen or pepsin solubilized and/or soluble collagen. The collagen can be from mammalian cells synthesized in vitro. The collagen can be from molecularly engineered constructs and synthesized by bacterial, yeast or any other molecularly manipulated cell type. For example, the collagen can be sea cucumber dermis collagen, bovine, caprine, porcine, ovine or other suitable donor mammal, marine animal collagen such as chinoderms, molecularly engineered collagen, or gelatin (e.g., in any suitable form including solid, gel, hydrogels, liquids, or foams). In addition, the collagen can be digested with a protease before, where used, oxidizing and polymerizing steps. The collagen can be in the form of microfibrils, fibrils, natural fibers, or synthetic fibers.

In some embodiments, the collagen can be solubilized, dissolved or otherwise transferred into an acid solution, for example, acetic acid (e.g., about 0.01M to about 1.0M, typically about 0.5M), hydrochloric acid (between about pH 1 to about pH 3, typically about pH 2.0), or any other suitable acid at appropriate concentration (e.g., about pH 1.0 to about pH 3.0, typically about pH 2.0). Dialysis may optionally be used to neutralize a soluble collagen solution. The collagen can also or alternatively be dissolved in a neutral buffered solution either with or without salts, e.g., phosphate buffer at about pH 7.0, or phosphate buffered saline at about pH 7.0. The phosphate buffer can be at any concentration of sodium phosphate between about 0.01 and 0.5, but more typically between about 0.02 and about 0.1M. The buffer can also be any buffer, including, but not limited to, for example, sodium acetate, HEPES, or MOPS. The collagen can be present in a quantity that is at least about 0.1% to about 10%, typically between 0.1% to about 5% (e.g., about 0.1, 0.2, 0.3, 0.4, 1.0, 2.0, 4.0%) by weight per volume or by weight per volume in the neutral buffer solution before fibrillogenesis and fiber formation. In a dried fiber collagen, collagen can be present in an amount of weight by volume of between about 50-100% (e.g., at least about 75%, 90%, 95% or 100%) before crosslinking (where crosslinking is used).

Collagen "microfibrils," "fibrils," "fibers," and "natural fibers" refer to naturally-occurring structures found in a tendon. Microfibrils are about 3.5 to 50 nm in diameter. Fibrils are about 50 nm to 50 µm in diameter. Natural fibers are above 50 µm in diameter. A "synthetic fiber" refers to any fiber-like material that has been formed and/or chemically or physically created or altered from its naturally-occurring state. For example, an extruded fiber of fibrils formed from a digested tendon is a synthetic fiber but a tendon fiber newly harvested from a mammal is a natural fiber.

In some embodiments, other materials may be used with the collagen fibers to form an elastic construct. For example, non-cytotoxic (and typically non-inflammatory) polymers including thermoplastic materials and/or polymers based on monomers such as acrylates, e.g., polymers which are prepared by copolymerizing two or more of the monomers such as alkyl acrylate monomers (alkyl moiety containing preferably 1 to 12, more preferably 1 to 6, carbon atoms) (e.g., methyl acrylate, ethyl acrylate, butyl acrylate or octyl acrylate); alkyl methacrylate monomers (alkyl moiety containing preferably 1 to 6, more preferably 1 to 4, carbon atoms) (e.g., methyl methacrylate or ethyl methacrylate); acrylic acid or methacrylic acid; vinyl cyanide monomers (e.g., acrylonitrile or methacrylonitrile); aromatic vinyl monomers (e.g., styrene or a-methylstyrene); and vinyl halide monomers (e.g., vinyl chloride or vinyl bromide). In addition to the monomers, cross-linking agents such as divinylbenzene, monoethylene glycol dimethacrylate and polyethylene glycol dimethacrylate may be used alone or as a mixture of two or more. Of these alkyl acrylate monomers, alkyl methacrylate monomers and aromatic vinyl monomers may be particularly suitable as the monomers, with a combination of an alkyl acrylate monomer and an alkyl methacrylate monomer. Combinations of an alkyl acrylate monomer and an aromatic vinyl monomer for the biocompatible thermoplastic material may be useful, including, but not limited to, a combination of butyl acrylate and methyl methacrylate and a combination of butyl acrylate and styrene.

The synthetic collagen fibers and/or polymeric and/or thermoplastic materials can include other non-collagenous components or biocompatible materials, such as therapeutic agents. The term "therapeutic agent" means biologically active agents, drugs and/or compounds for generating a clinical therapeutic effect. Examples of such agents or drugs include, but are not limited to, particulates, hydroxyapatite and other mineral phases, or drugs that facilitate tissue growth, inhibit inflammation, treat infections, reduce pain, thin blood, inhibit coagulation, blockage, plaque build up or provide other desired therapies or effects, including, in some embodiments heparin and/or growth hormones. See also, U.S. Pat. No. 6,821,530, incorporated herein by reference above. For example, the fibers and/or constructs formed from same, can include compositions that can contain carbon nanotubes, zinc nano-wires, nano-crystalline diamond, or other nano-scale particulates; and larger crystalline and non-crystalline particulates such as calcium phosphate, calcium sulfate, apatite minerals. For example, the compositions can also or alternatively contain therapeutic agents such as bisphosphonates, anti-inflammatory steroids, growth factors such as basic fibroblast growth factor, tumor growth factor beta, bone morphogenic proteins, platelet-derived growth factor, and insulin-like growth factors; chemotactic factors such fibronectin and hyaluronan; and extracellular matrix molecules such as aggrecan, biglycan, decorin, fibromodulin, COMP, elastin, and fibrillin. In some embodiments, the fibers and/or fiber-derived constructs can contain cells, engineered cells, stem cells, and the like. Combinations of the above or other materials can be embedded, coated and/or otherwise directly or indirectly attached to the collagen fibers (such as in the liquid polymeric material used to apply the film) and/or construct formed of same.

The collagen fiber can be formed from a collagen gel that includes collagen fiber, fibrils and/or microfibrils, typically dermal collagen, that has been acid or pepsin solubilized (e.g., soluble collagen) and processed to maintain the collagen in its molecular form. The collagen concentration of the soluble collagen and/or resulting soluble collagen gel can be between about 0.1% to about 4% weight per volume. The soluble collagen gel may be formed to be in a cylindrical shape of a defined length and diameter, typically with a diameter of between about 0.1 to 1 cm, and a length of between about 5 cm to about 100 m, more typically with a length between about 1 m to about 100 m, such as a length between about 10 m to about 50 m, which is subsequently dried to form a collagen fiber.

The collagen fibers and collagen gel can be produced in batch or continuous-type systems, including wet gel collagen extrusion systems, which produce cylindrical lengths of gel that can be allowed to substantially dry (actively or passively) to obtain a suitable length of fiber. Examples of some collagen fiber production processes that can generate soluble collagen in suitable lengths are described in U.S. Pat. No. 6,565,960, and pending U.S. Patent Application Publication No. US-2008-0188933-A1, the contents of which are hereby incorporated by reference.

The collagen fiber(s) can be spooled (e.g., held wound on a spool) for supplying to an automated or semi-automated winder to form the biomedical construct and/or biomaterial. The spooled fiber(s) can be in a dry state or may be in a hydrated or partially hydrated state. The collagen fiber(s) may be formed with a relatively thin diameter, such as, for example, between about 0.05 mm to about 0.2 mm (average) (dry or wet), such as about 0.08 mm dry diameter (average) and/or about a 0.13 mm wet diameter (average). The at least one fiber on the spool for the winding can be formed as a single continuous length or may be formed with multiple fibers joined end-to-end or a single length to form a desired length for the winding.

It is noted that the present invention contemplates using various thermoplastic materials to provide the desired elasticity and can be non-cytotoxic (and typically also anti-inflammatory). For discussion purposes, the specification primarily describes acrylates but the invention is not intended to be limited to acrylates as the thermoplastic material. The use of acrylates are exemplary embodiments of the present invention.

In some embodiments, biocomposite materials contemplated by embodiments of the invention can be made from at least one collagen fiber and a non-cytotoxic polymeric material such as polyacrylate emulsions and/or other thermoplastic materials, and the collagen fiber(s) can be either cross linked or uncrosslinked. The polymeric material can be applied in a liquid state to the collagen fiber. In some embodiments, the liquid polymeric material can be a microemulsion. The polymeric material can further include one or more additives including surfactants, antioxidants, solvents, polymerization inhibitors, chain transfer agents, fillers, thickening agents, flow agents, polymerization initiators and accelerators, lubricants, air release agents, wetting agents, UV stabilizers, compatibilizers, fire retardants, urethane reaction catalysts, moisture scavengers, and shrink-reducing additives, and/or one or more therapeutic agent(s).

The acrylate emulsion can be homo or co-polymer based and may include small molecular weight constituents and/or compounds (typically water soluble). The biocomposite material can have multiple applications in the medical field as a biomaterial, such as for artificial tissue or other application including wound care and treatment. The resulting biomaterials can be an elastomeric material with structural integrity and/or sufficient strength for its target use. The biomaterials can have a controlled elasticity suitable for elastic tissue repairs, including, but not limited to, elastic vessel replacements, elastic skin or wound repairs or replacements, lung tissue repairs or reinforcements, and cardiac tissue repairs or reinforcements. Embodiments of the invention provide biomaterials that have a "memory shape" structure so that after elastically deforming, the material substantially returns to an original shape or configuration without damaging the structural integrity and functionality of the material. The biomaterials can be configured to cycle through a number of stress/relaxation cycles sufficient to provide the desired therapy and corresponding to the target use. The biomaterials can substantially simulate or correspond to the mechanical properties (elasticity) of natural "healthy" or normal tissue elasticity and structure.

The biomaterials can be provided and/or formed by any suitable process or method into various arrays including but not limited to, braids, weaves, twists, knits, parallel arrays, and the like, with various patterns of fiber(s) in various orientations and fiber density (dense to sparse and tight to loose geometries) to meet the desired mechanical properties for the target use.

The term "film" refers to a thin layer of a coating material. The film is typically present in a thickness that is between about 5 microns to about 5 mm. The film may embed the collagen fiber(s) so as define a combined biocomposite material with a thickness of between about 0.5 mm to about 6 mm thick, typically between about 1 mm to about 5 mm (average, dry). The film may be permeable and flexible. In some embodiments, the film may be permeable to only small ions or low molecular weight (<150 g/mol) compounds. The film may be optically transmissive, e.g., translucent or transparent, or may be opaque. Several layers of the same or different polymeric materials (e.g., one or more polyacrylate emulsions of the same or different formulations) can be applied to generate the desired coating thickness or coverage. The color or transmissive characteristics may change when hydrated. The coating can infuse into, permeate, migrate and/or embed a collagen fiber to form a collagen fiber laminate and/or to encase the collagen fiber. The coating can form a film that may prevent swelling and resulting deformation of the device upon hydration. The coating/film may provide a smooth (and typically a substantially constant diameter) dry surface over or under the fiber and extend over the interstitial space of the fiber(s) to close the outer and/or inner surface of the construct. For example, the coating can form a non-cytotoxic thermoplastic material, e.g., polyacrylate film that embeds the fiber (s) and extends as a solid film over interstitial spaces of the fiber mesh. The fluid polymeric material can help the fiber(s) retain its wound shape (e.g., inhibit unraveling) during and/or after winding. The film and collagen can give the construct reversible elasticity and sufficient mechanical properties such as modulus of elasticity and/or structural strength.

Figure 1B:
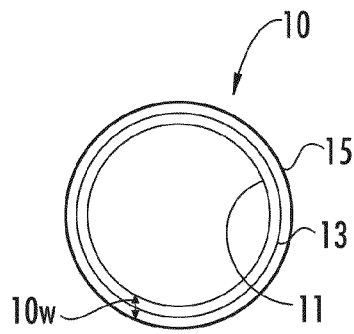
FIG. 1B is a schematic end view illustration of the cylindrical construct shown in FIG. 1A according to some embodiments of the present invention.

Referring now to the figures, FIG. 1A, an exemplary elongate construct 10 is shown on a support member 20. As shown in FIG. 1B, the construct 10 includes an inner biocompatible thermoplastic material (e.g., polyacrylate) coating layer 11, an intermediate layer of at least one wound collagen fiber 13, and an outer biocompatible thermoplastic material (e.g., polyacrylate) coating layer 15. The thermoplastic material (e.g., polyacrylate) can embed and/or encapsulate (seal) the fiber(s) 13. In other embodiments, the construct 10 can be formed without one of the inner 11 and/or outer layer 15 and/or may optionally include other materials or constituents and/or layers. As shown in FIG. 1B, the construct 10 can have a wall 10*w* with a suitable thickness defined by the at least one collagen fiber 13 and the layers 11, 15 (where used) and/or other coatings or materials placed thereon. The construct 10 can have an open through cavity or may be filled or partially filled with a blood-thinning media and/or anticoagulant agent or other therapeutic material (e.g., an anti-inflammatory, antibiotic and/or the like).

As also shown in FIG. 1A, the at least one collagen fiber 13 has an angular fiber pattern 13*p* (or fiber mesh) of repeating intersecting collagen fiber segments along its length. The angular pattern 13*p* can be defined by a number of revolutions of the at least one fiber 13 about the support member 20 at a given pitch or pitches for at least one layer (typically more than one layer). The at least one collagen fiber 13 is wrapped or wound about the support member 20 exterior surface to form a desired shape. The support member 20 can be any suitable shape (shown as cylindrical in FIG. 1A) and may vary in shape and/or size over its length (not shown). As shown in FIG. 1A, the at least one fiber 13 may be wrapped a plurality of times about one physical space to form a reinforced location 52, shown as a reinforced end portion (and the reinforced portions can also be at any intermediate or internal locations). A clinician can secure a suture or other anchoring member to the reinforced end portion for attachment to local tissue. However, other attachment members and/or types may be used including, for example, biocompatible adhesives, staples, screws, nails, rivets, bone anchors and the like and combinations thereof.

The polymeric material (e.g., polyacrylate emulsion) can be applied to the collagen fiber(s) 13 during fabrication (e.g., a winding, weaving or braiding operation). The polymeric material can be applied to the rod before the fiber winding step. The polymeric material can be applied in a fluid state. The combination of the polymeric material with the collagen fiber(s) 13 yields a composite biomaterial with controlled elasticity suitable for elastic vessel replacements or other elastic repairs, while the collagen fiber(s) can provide rigidity and/or strength suitable for pressure-loading applications.

Hydration of the composite biomaterial can generate a higher degree of elasticity, typically without loss of structural integrity or strength. The dry biocomposite product is able to absorb a relatively large amount of liquid, e.g., about its body weight in water or exudates for wound bed applications.

Figures 2A, 2B:
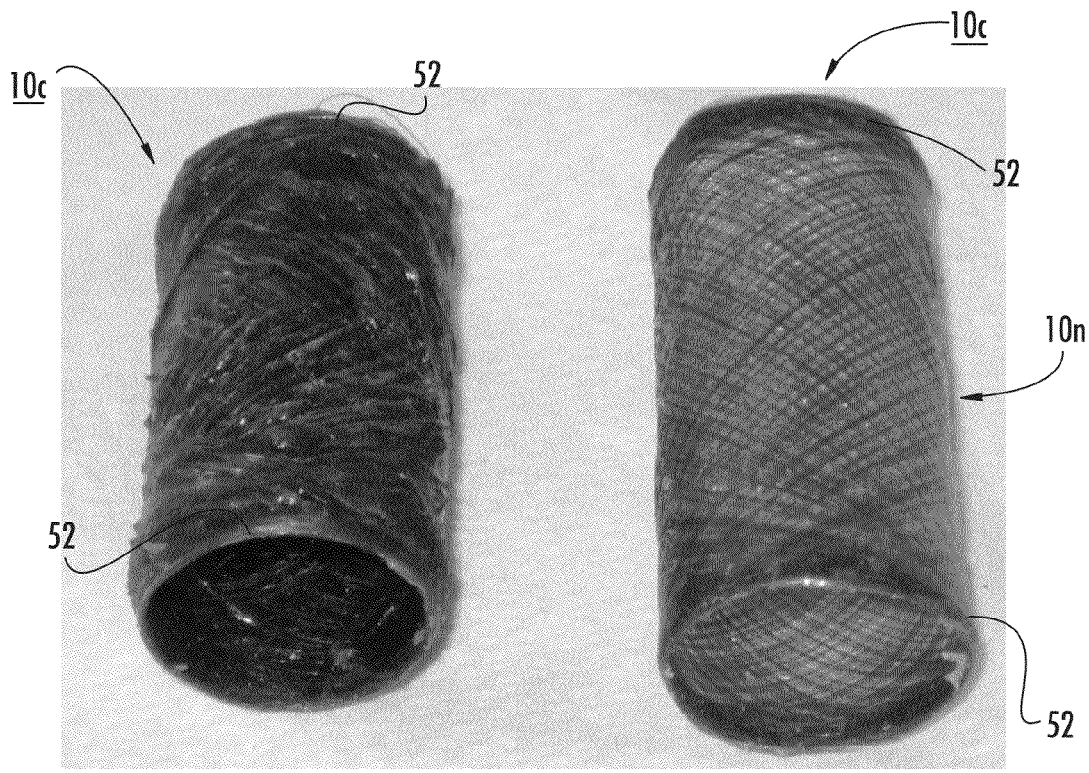
FIG. 2A is a top perspective digital photograph of a multi-fiber construct according to embodiments of the present invention.
FIG. 2B is a top perspective digital photograph of a single fiber construct according to embodiments of the present invention.

FIG. 2A illustrates an exemplary multi-fiber device 10*c* (as shown, seven fibers) in a cylindrical shape. FIG. 2B illustrates an exemplary single-fiber device 10*e* also in a cylindrical shape. As shown, both include the reinforced end portions 52. The cylindrical configurations may be particularly suitable for artificial vessels and vascular tissue (see FIG. 8).

The construct 10 can have reversible elasticity with sufficient rigidity or strength to prevent collapsing under pressure while allowing flexibility sufficient to allow the construct 10 to expand and contract with changes in blood pressure. The vascular graft can be tailored to a wide range of inner diameters to suit multiple vascular replacements. The tubular construct 10 can be hydrated prior to surgical application as the dry construct is able to absorb a relatively substantial amount of water (typically about its body weight) in an aqueous (blood) environment. The dried tube can be used "as-is" (used in a non-cross-linked state and hydrated when in the body or prior to placement in the body). In other embodiments, the collagen fiber(s) can be cross-linked with any agent or action that cross-links the collagen, typically prior to the fabrication (e.g., winding step or before the liquid polymer is added to the fiber(s)). The collagen fiber(s) may be cross-linked with nordihydroguaiaretic acid (NDGA), see, e.g., U.S. Pat. No. 6,565,960, and U.S. Patent Application Publication No. US-2008-0161917-A1, the contents of which are hereby incorporated by reference as if recited in full herein.

Constructs of this and other embodiments can be used for other repairs or treatments as will be discussed further below. The construct 10 is non-cytotoxic and may be biocompatible and, in particular embodiments can be configured to provide a desired half-life or other suitable life for its intended function.

The construct 10 and/or the fiber 13 can optionally be cross-linked with a suitable polymerizing material, such as, but not limited to, NDGA, or the collagen fiber(s) may be used in the construct in a non-cross-linked state. The NDGA cross-linking of the collagen fiber(s) increases the strength of the device 10. In some embodiments, the collagen fiber 13 is not cross-linked during the winding process.

In some embodiments, the collagen fiber(s) can be cross-linked with NDGA before the winding step. In particular embodiments, the winding can be carried out using both (a) one or more uncrosslinked collagen fibers and (b) one or more cross-linked collagen fibers, such as one or more NDGA cross-linked collagen fibers.

Figure 3A:
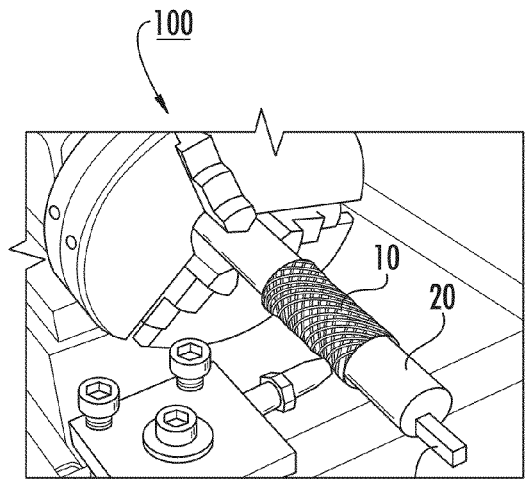
FIG. 3A is a top perspective view of a system for producing a wound fiber construct according to some embodiments of the present invention.
Figure 3B:
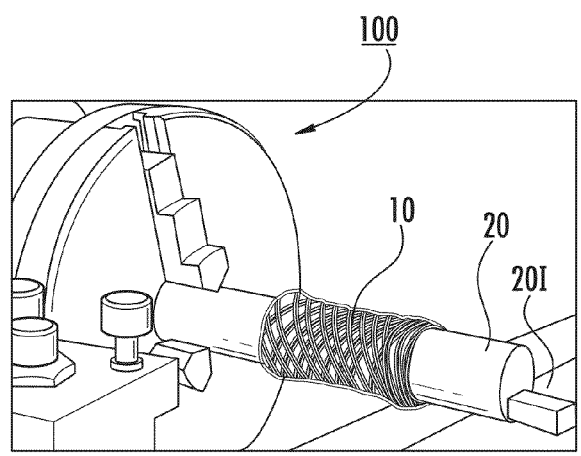
FIG. 3B is a side perspective view of the system shown in FIG. 3A.
Figure 3C:
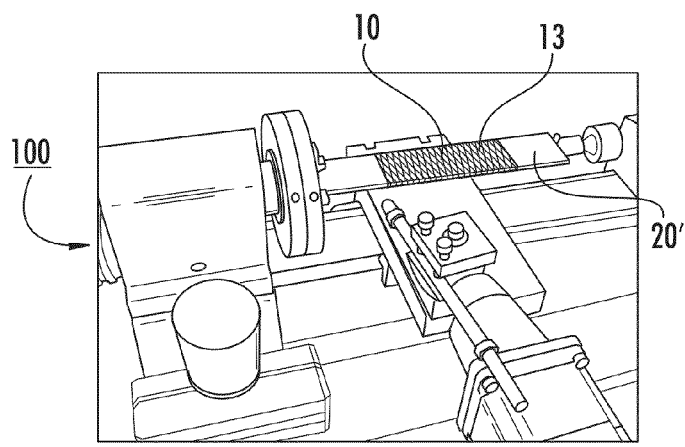
FIG. 3C is a side perspective view of the system shown in FIGS. 3A and 3B but with a planar elongate support member according to some embodiments of the present invention.

As shown in FIGS. 3A-3C, the construct 10 can be made by winding at least one collagen fiber 13 about a support member 20 using a computer-guided and/or controlled lathe system 100. The support member 20 can be tubular, e.g., cylindrical, as shown in FIGS. 3A, 3B or may be substantially flat and rectangular as shown in FIG. 3C. Other geometries may also be used, such as, for example, a frustoconical or funnel shape. Typically, the support member 20 is elongate and has a substantially circular, oval, polygonal or other cross-sectional shape.

The at least one collagen fiber 13 can be provided with one or more polymeric (e.g., thermoplastic) layers 15 before, during and/or after winding the at least one collagen fiber 13 to seal the fiber(s) 13 within the biocomposite material and/or to form a smooth inner and/or outer surface of the construct 10. An example of a small lathe, typically a micro or miniature lathe, suitable for fabricating embodiments of the constructs, is the Model 4410 lathe available from Sherline Products, Inc., having a place of business in Vista, Calif. The system 100 can include two user-selectable inputs to operate the lathe system: one controls the speed at which the support member spins and the other controls the pattern (fiber angle) in which the at least one fiber 13 is laid and/or fed onto the support member 20. The winding operation can be configured so that the fiber(s) 13 is self-pulling from a spool of collagen fiber(s) based on the speed of the spinning support member 20. The feeder head can have a channel that holds the fiber(s) and directs the fiber(s) to wrap/wind about the support member 20. The lathe can co-wind a plurality of fibers or fiber bundles substantially concurrently about the support member 20. In some embodiments, a plurality of spools of collagen fibers can supply fibers that can be applied concurrently to the support member 20 as a single bundle of fibers or as separately wound fibers or fiber bundles.

The winding can be performed so that at least one layer of the at least one collagen fiber 13 has a substantially constant pitch for at least a major portion of a length thereof or so that at least one layer of the at least one collagen fiber 13 has a variable pitch for at least a major portion of a length thereof.

The support member 20 can include a lubricious and/or smooth surface. The support member 20 can include an embossed surface that provides a smaller contact surface area. The support member 20 can comprise or be formed of a polymer material. In other embodiments, the support member 20 can include an anti-slip surface with ridges or a sleeve can be placed over the support member (not shown) to contact the next layer (e.g., inner film 11 or fiber 13). In some embodiments, the support member 20 comprises Teflon® or other suitable low friction and/or anti-stick material and the polymeric coating can adhere the fiber (e.g., be a "sticky" substance) to the support member 20 during the winding operation to inhibit movement on the member 20 once applied.

The support member 20 can be configured to facilitate removal of the construct 10. For example, the construct 10 may be wound snugly and/or tightly against the outer surface of the support member 20 and allowed to dry. The support member 20 can be configured to reduce in cross-sectional size or disassemble with the construct 10 held thereon to allow easy removal of the elongate construct. In some embodiments, the support member 20 can be a multi-piece device that provides this size change. In other embodiments, the support member 20 may be cooled while the construct is heated to provide a size difference. In particular embodiments, the support member 20 can cooperate with an insert 201 (FIGS. 3A, 3B) that provides the desired size adjustability. The removable insert 201 can be placed in the support member 20 (e.g., Teflon® rod) so that, when removed, a gap is formed between the rod and the construct to facilitate easy sliding removal of the construct 10 from the support member 20. In other embodiments, the construct 10 can be removed from the support member without such a size adjustment, e.g., its inner surface may be sufficiently lubricous or a suitable liquid or other material can be used to slide the construct off the support member. In some embodiments, the construct 10 can be cut in a lengthwise or longitudinal (e.g., "X") direction and taken off the support member 20.

FIG. 4 illustrates that different fiber 13 configurations may be used for the winding operation/method or to form the construct 10. Examples of fiber configurations include a single fiber $13_1$, a plurality of fibers $13_1$-$13n$ (typically n=2 to 100) that can be concurrently co-wound about the support member 20, a fiber bundle 13b, a series of discrete shorter fibers joined to form a desired length for winding 13j, and a twisted, woven or braided fiber bundle 13t. For the fiber bundles 13b, 13t, two or more fibers 13 can be grouped together to form the fiber bundle 13b, 13t and that bundle 13b, 13t applied or wrapped about the support member 20, similar to a single fiber. One or more fiber bundles 13b, 13t may be used to form the construct 10. Combinations of the different fiber types may also be used for some constructs 10. That is, for example, a twisted fiber 13t can be co-wound with a single fiber $13_1$ and/or a single fiber $13_1$ may be used to form one layer and a twisted 13t to form a different layer, and the like.

The collagen fiber(s) 13 can be wound using various fiber angles (e.g., pitch angles), such as angles between about 1-90 degrees, typically between about 5-60 degrees, such as, for example, 5, 10, 15, 20, 25, 30, 35, 40, 45, 50, 54 and 55 degrees, or other odd or even numbers between 5-70. Where constructs of multiple layers are used, one layer may have a first pitch and another layer may have a different pitch. The patches may be formed with winding angles of between about 5-30 degrees while the tubular constructs may have winding angles of between about 1-90 degrees, typically between about 5-90 degrees.

FIG. 5A illustrates that a construct 10 can be wound with increased fiber density 52 along certain segments, typically forming end rings 52r. However, the increased fiber density 52 can also reside at other locations along the construct 10. This increased fiber density 52 can provide sufficient rigidity to allow a suture to attach thereto. As shown in FIG. 5A, the construct 10 is tubular 10t and may optionally include an increased density segment 52 at an intermediate location. FIG. 5B illustrates that the construct 10 can be used as formed, or may be cut or separated along a Y-axis into two components 10ta, 10tb. For the latter, the intermediate increased density ring 52 can form end rings for the separated construct 10ta, 10tb.

FIG. 6A illustrates a construct 10 that has a wound fiber(s) 13 and is relatively flat 10f and/or rectangular. Again, the construct 10f can optionally include increased fiber density segments 52 that may be suitable for end rings 52r. FIG. 6B illustrates that the construct 10f can be cut along the X-axis and separated into at least two components that form biocompatible patches. The intermediate increased density ring(s) 52, where used, can optionally form end rings 52 for the separated construct 10fa, 10fb, and the like.

Figure 7:
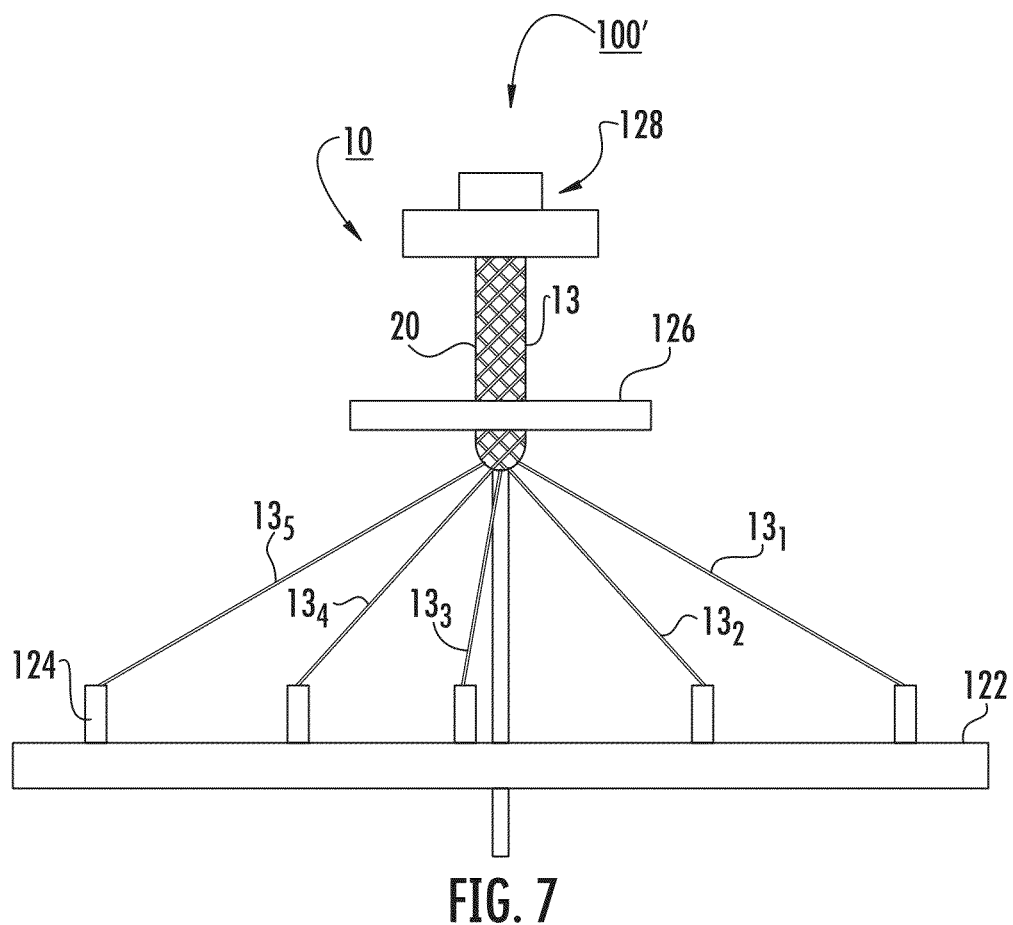
FIG. 7 is a front view of a winding apparatus that can be used to wind collagen fiber according to embodiments of the present invention.

FIG. 7 illustrates an example of another automated winding system 100' that can be used to form the construct 10. This embodiment uses several fibers 13, each independently wound and/or wrapped to weave or braid the fibers about the support member 20 to form the construct 10. The system 100' includes a plate 122 supporting spindles 124, a forming plate 126, a support member (shown as a cylindrical mandrel) 20 that extends through an aperture in the forming plate 126, and braid puller 128. An exemplary microbraider is believed to be available from Kokubun Ltd of Japan. See also, FIG. 2 and col. 2 of U.S. Pat. No. 7,135,040, the content of which is hereby incorporated by reference.

The at least one fiber 13 can be wound after cross-linking and the fiber(s) may not be cross-linked at all. The fiber(s) 13 can, where desired, be polymerized with any suitable cross-linking materials, to promote collagen organization, such as, for example, NDGA, but other cross-linking materials may be used, including, for example, glutaraldehyde. The collagen fiber can also be treated with other methods to improve the tensile properties of the fiber. The (typically dry) collagen fibers 13 can be cross-linked with agents such as glutaraldehyde, formaldehyde, epoxy resins, tannic acid, or any other chemical agent that produces covalent cross-links between collagen molecules within fibrils or between fibrils. Alternatively, the at least one fiber 13 can be treated to induce cross-linking between collagen molecules such as, but not limited to, one or more of a carbodiimide treatment, ultraviolet irradiation either with or without carbohydrates to initiate glycation adducts, and dehydrothermal treatment coupled with any of the aforementioned methods and/or agents.

Figure 8:
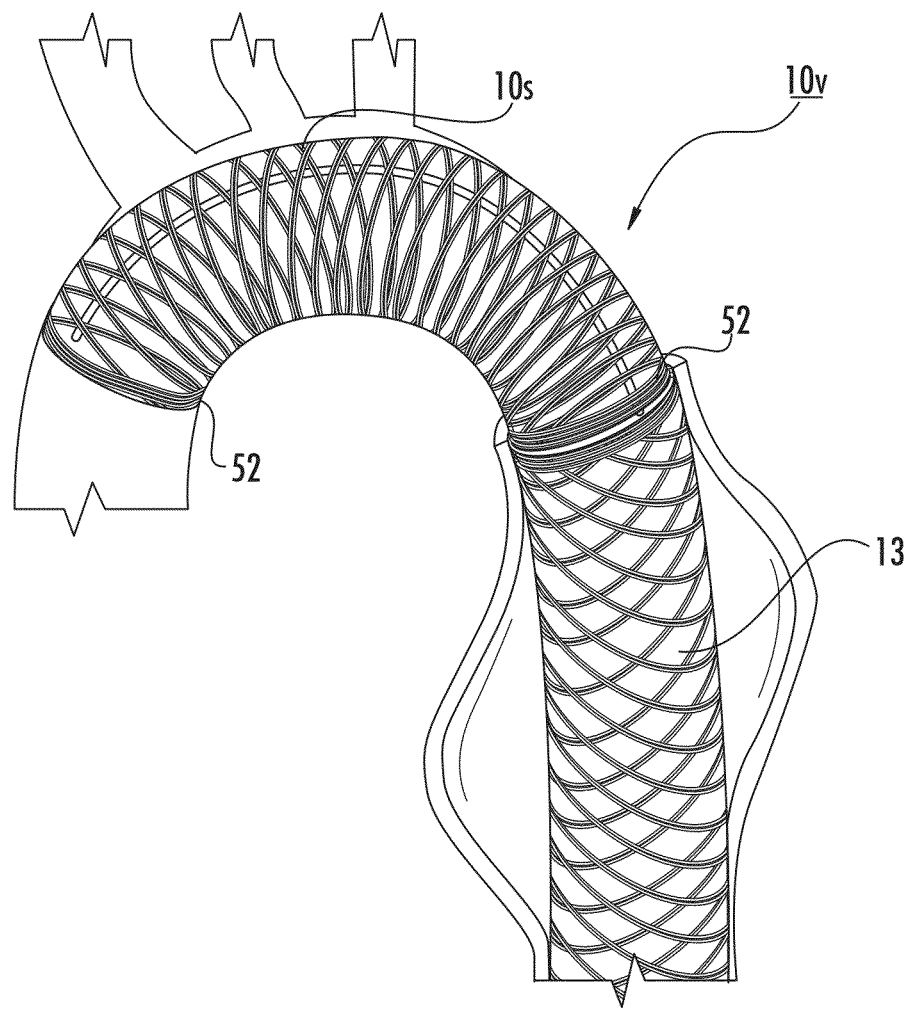
FIG. 8 is a schematic illustration of an artificial vessel according to embodiments of the present invention.

FIG. 8 illustrates that the cylindrical construct 10 may be particularly suitable as a vessel 10v for vascular prosthesis such as for aortic stents and/or vessels for repairing or replacing veins or arteries. In some embodiments, the vessels 10v may be used for blood vessels such as coronary or other lumen vessels. The vessels 10v can have diameters between about 1 mm to about 12 mm. In some embodiments, the blood vessels can be for repair, replacement or use of small lumen vascular vessels, typically about 6 mm or less in diameter. The construct 10 is tubular with an open cavity and has a flexible elastic configuration to be able to expand and contract responsive to blood flow and pressure and may be able to mimic a natural behavior of normal "healthy" blood vessels in an environment of pulsatile flow.

The vessel 10v can be formed using at least one fiber 13. In some embodiments, the vessel 10v can be formed of a single fiber wound in multiple overlying layers. The fiber 13 can be a continuous length of a single fiber or the fiber 13 can have a length provided by a series of shorter fibers attached in an end-to-end orientation.

As noted above, the collagen fiber length used for forming the vessel 10v can be any suitable length, typically between about 1 cm to about 100 m, and more typically between about 1 m to about 100 m. In some particular embodiments, the vessel 10v can be formed with a fiber length that is between about 5 m-20 m, such as between about 8-12 m. Each vessel type may use a different length of fiber. The vessel 10v can be formed using a single fiber 13 of a continuous length that is wrapped in several layers about the support member 20. Use of a single fiber 13 can reduce the likelihood of any fraying associated with multiple fibers (such as those wound in one lengthwise direction). The vessel 10v can have a length that is between about 2 cm to about 8 cm (or more). The vessel 10v can have an inner diameter that is between about 1-12 mm with the wall thickness (on average or measured at a thickest part) being about 0.1 mm to about 2 mm. The vessel 10v may optionally have a slit 10s in a portion of a lengthwise direction to allow for ease in placement. One or both end portions of the vessel 10v may have an increased density of wound collagen fiber 52. An intermediate portion may also optionally include an increased density region 52. The vessel 10v can be formed by cutting or otherwise separating a longer tubular construct into a desired vessel length without fraying.

Figure 9:
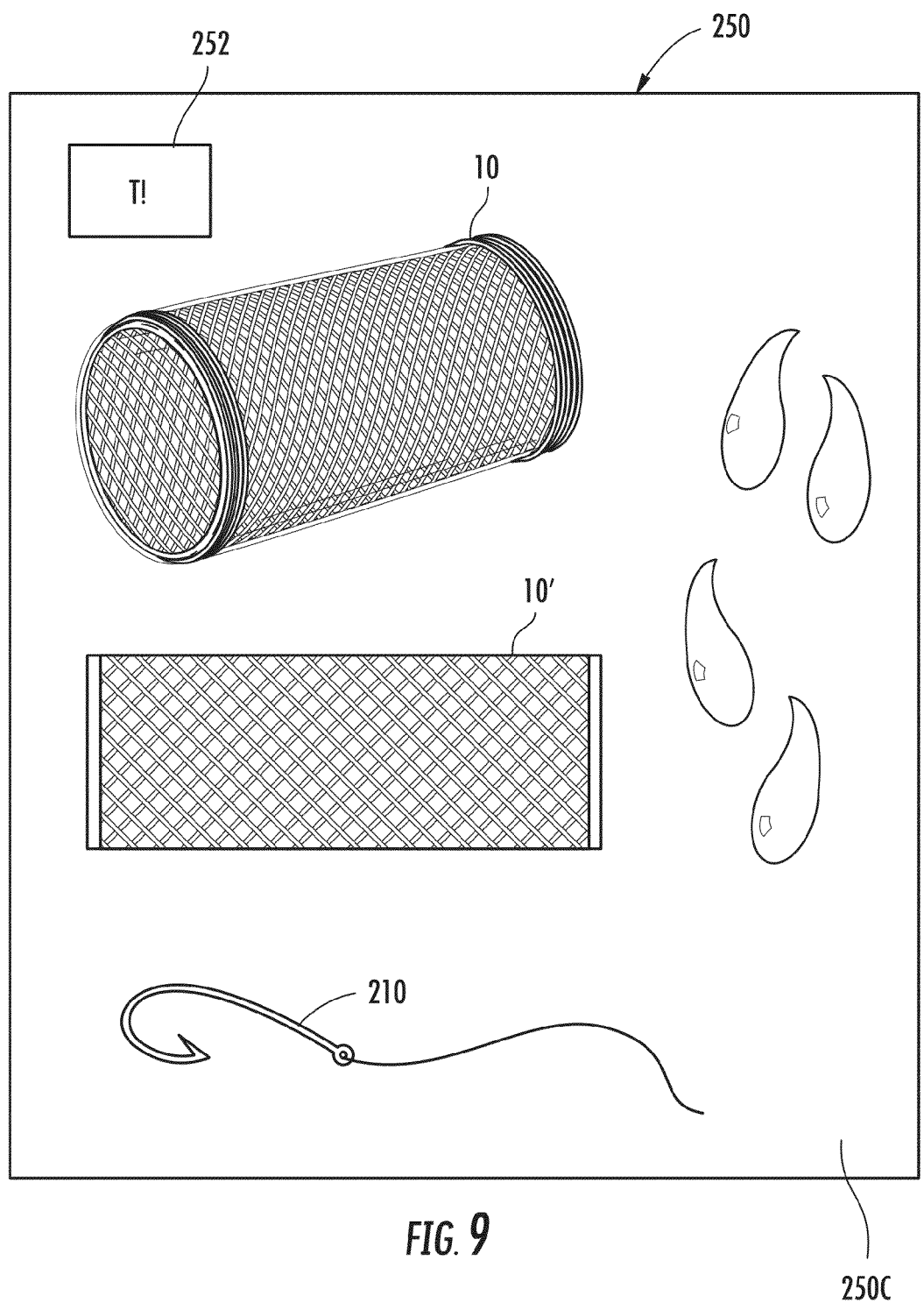
FIG. 9 is a schematic illustration of a medical kit according to embodiments of the present invention.

FIG. 9 illustrates a medical kit 250 that includes a construct that is medical device or implant 10 or 10'. The kit 250 may optionally include other components, such as, for example, a container of surgical adhesive, sutures 210, suture anchors, and the like. The device or implant 10, 10' may be held hydrated in a flexible sealed package of sterile liquid 230. The kit 250 may include a temperature warning so that the construct 10, 10' is not exposed to unduly hot temperatures that may degrade the implant. A temperature sensor 252 may optionally be included on the package of the kit to alert the clinician as to any excessive or undue temperature exposure prior to implantation. For example, it may be desirable to hold or store the kit 250 (and implant or device 10, 10') at a temperature that is less than about 37° C. and/or 100° F. prior to implantation. The implant 10, 10' can be stored dry and hydrated prior to use or may be packaged in a hydrated state. The kit 250 may be packaged in a housing with a temperature controlled or insulated chamber 250c to facilitate an appropriate temperature range.

Figure 10:
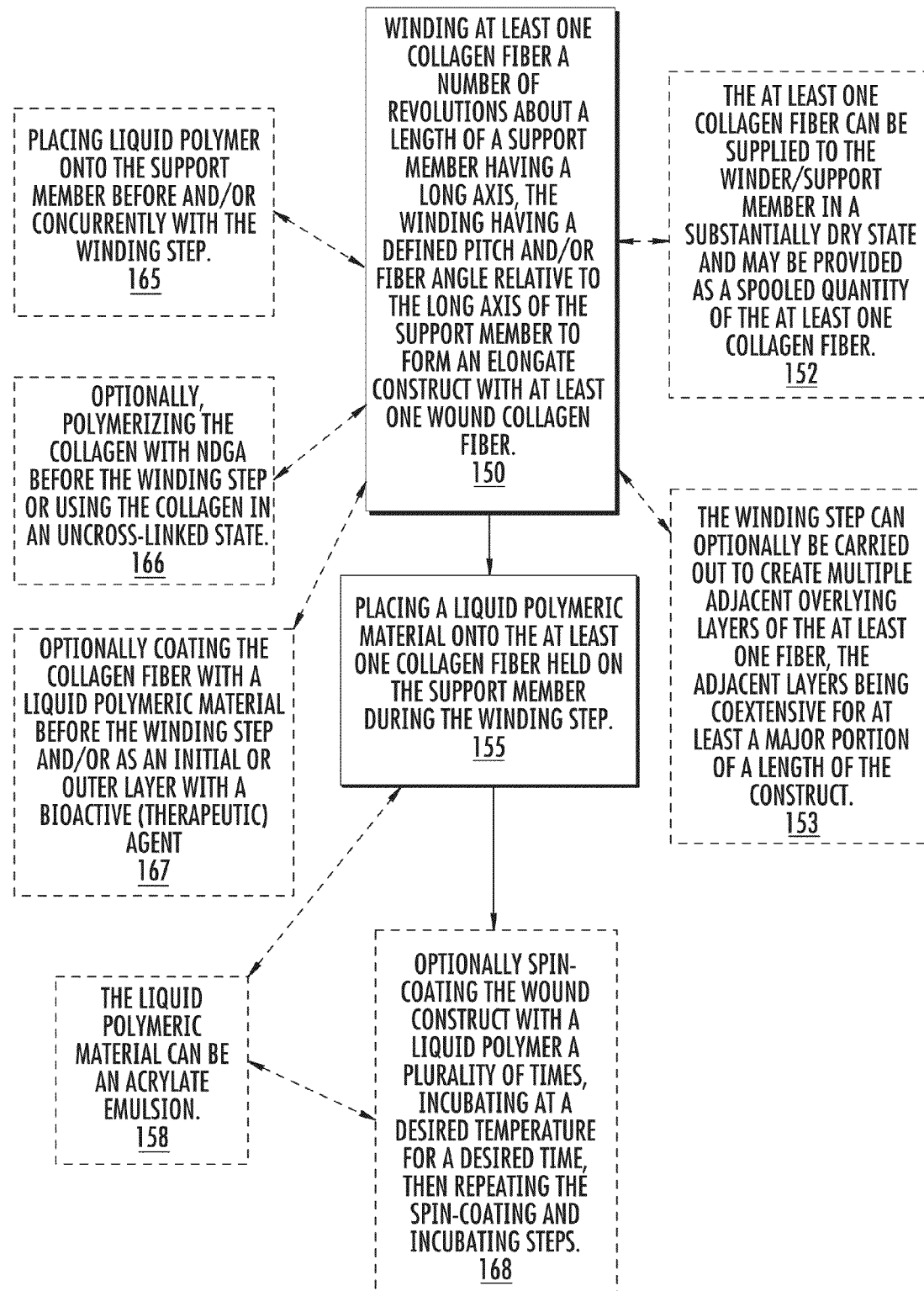
FIG. 10 is a flow chart of operations that can be used to fabricate a construct according to embodiments of the present invention.

FIG. 10 is a flow chart of operations that can be used to carry out embodiments of the present invention. In some embodiments, the at least one collagen fiber is wound a number of revolutions about a length of a support member having a long axis. The winding can have a defined pitch and/or fiber angle relative to the long axis of the support member to form an elongate construct with at least one wound collagen fiber (block 150). The winding step can form multiple overlying layers of the at least one collagen fiber in one or more fiber angles so that the at least one fiber intersects itself at different locations along a length of the construct.

A polymeric material can be applied to and/or placed on the at least one collagen fiber held on the support member during the winding step (block 155). The polymeric material can be applied in a fluid (typically a liquid) state. In some embodiments, as the fiber(s) is wound about the support member, the (liquid) polymeric material, e.g., acrylate emulsion, can be substantially continuously applied (e.g., wrapped, painted, sprayed, dripped, poured, brushed and the like) onto the fiber(s) so that the fiber(s) is wetted while one or more layers are wound on the lathe. Where used, the acrylate emulsion can act as a "sticky" substance that adheres the collagen fiber in position on the support member during the winding process. The polymeric material can optionally comprise a polyacrylate emulsion (block 158).

The at least one collagen fiber can be supplied to the winder/support member in a substantially dry state and may be provided as a spooled (dry) quantity of the at least one collagen fiber (block 152). The fiber(s) can be supplied and wound in a non-cross-linked state.

In some embodiments, the winding step can be carried out to create multiple adjacent overlying layers of the at least one fiber, the adjacent layers being coextensive for at least a major portion of a length of the construct (block 153). That is, for example, the winding can wind back and forth over the support member to create overlapping layers of the at least one fiber and each layer can have substantially the same length (such that the layers are substantially coextensive with each other) or one or more of the different layers may have different lengths.

Optionally, additional layers of the same or a different (liquid) polymeric material can be onto the at least one wound collagen fiber to cover at least the outer surface in a film that extends over the interstitial spaces of the fiber(s) and can provide a coating. The additional (e.g., acrylate) material can be applied by spin coating the wound construct as it remains on the support member 20 (typically between two to three times), then incubating the construct at a desired temperature, such as between about 37-40° C., typically about 37° C., for a defined time, typically between 2-24 hours, such as about 4 hours (block 168). The spin-coating and incubating steps can be repeated one or more times. After the final spin-coating or last outer layer is applied, a longer incubation time may be used, e.g., the earlier incubation times can be between 2-8 hours and the "final" incubation can be longer, e.g., between 8-24 hours, typically overnight (where multi-shift production is not used). Other post-winding coating methods may be used. The spin-coating and winding steps and the outer layer formation step (where used if different from the spin-coating) can be carried out using the same material and/or emulsion formulation or different polymeric materials. In some embodiments, the applying and spin-coating steps both use a polyacrylate emulsion.

Additionally or alternatively, an external heat source (e.g., a heat lamp) can be used to shorten the time used for drying the initial and/or supplemental polymeric coating(s) and/or thicker emulsions can be provided during the winding fabrication process to reduce the number of coats applied after the winding process.

Optionally, the collagen fiber can be polymerized before the fiber is wound or the collagen fiber can be provided and wound in an un-crosslinked state (block 166). In addition, the collagen fiber(s) can be coated with the same or a different liquid polymeric material before the winding step and/or as a final outer layer or emulsion or as an initial inner layer that can contain active biomolecules (e.g., heparin, growth factors, etc. . . . (block 167).

As shown in FIG. 11, the winding can be carried out so that the at least one fiber turns about the support member in one of a clockwise or counterclockwise direction along a first lengthwise direction for a first layer, then reverses to an opposing lengthwise direction and continues to turn about the support member in the same clockwise or counterclockwise direction for a second adjacent layer (block 180).

In some embodiments, the winding step has a first pitch for the winding of the at least one collagen fiber on the first layer and a second smaller or greater pitch for the winding of the at least one collagen fiber on the second layer. In some embodiments, the at least one fiber on the second layer resides between gaps defined by the at least one fiber wound with the defined pitch on the first layer.

The method can include cutting the construct in an axial direction to form a substantially flat collagen fiber patch. The method can include winding the collagen fibers in a plurality of axially spaced apart segments with increased collagen fiber density, at least some of which are provided as reinforced segments for suturing. The reinforced segments can be formed at end portions of the tube and optionally at one or more intermediate locations therebetween. The methods can produce an artificial vessel with the ability to expand and contract in response to blood flow therethrough.

Embodiments of the invention can be used for a number of different medical applications, including, but not limited to, wound bed patches, muscle or organ patches, cardiac patches, valve replacements or repairs, hernia patches, skin patches, burn treatment patches, skin/tissue repair patches or cuffs, blood vessel (artery, vein, and the like) repairs, sleeves that can reside about repairing tendon to prevent or inhibit adhesions, indwelling tubes for delivery of therapeutic agents, ducts such as lymphatic, hepatic, pancreatic and cystic ducts, tubes such as ureter and urethra tubes and nerve guides.

The present invention is explained in greater detail in the following non-limiting Examples.

Examples

Thus far, over 40 different devices have been manufactured using this new technique that combines collagen fibers with various water-based polyacrylate emulsions synthesized through a microemulsion polymerization. The combination of the NDGA-collagen fibers with the polyacrylate emulsion lends the novel properties observed for these devices for numerous biomedical applications, including, but not limited to, artificial elastic vessel and valve replacements. The polyacrylate emulsion has the ability to be synthesized in a one-step process and can optionally include covalently bound or encapsulated antibiotics and/or biologically active agents or compounds that may be incorporated into the devices during post-winding fabrication coating.

The collagen fiber was derived from dermal collagen that is acid or pepsin soluble. The soluble collagen can be made by neutralizing acid soluble collagen and keeping the soluble collagen at a desired low temperature to maintain the collagen in molecular form, (e.g., about 4° C.). Collagen concentration of the soluble collagen can be from about 0.1-4% weight per volume. The gel cylinder can be used in the gel form or allowed to dry, actively or passively (suspended in air), to form a collagen fiber having a diameter between about 0.05 mm (average) to about 0.2 mm (average).

As discussed above, the devices can be manufactured using an automated or semi-automated mechanical lathe. Some prototypes were made by winding a single 30 m-50 m long fiber onto a Teflon® rod with substantially continuous application of the emulsion. Continuous addition of the emulsion provides a sticky adhesive for the fibers to adhere to the Teflon® rod and remain where set on the rod and also can provide a water proof coating for the fiber that inhibits or prevents swelling and subsequent deformation of the device upon hydration.

The pitch of the fiber relative to the long axis of the tube can be specified. The thickness of the collagen winding can be adjusted, for example, corresponding to the number of layers of fibers that are laid on (and/or the number of fibers bundled together for the winding). During the fiber winding process, liquid acrylate is applied (e.g., painted) onto the surface of the laid-on fibers.

After the fiber has been wound for a sufficient time, such as between about 20-60 minutes, depending on the size and thickness desired, the mesh fabric is spin-coated 2-3 times with the emulsion, incubated at 37° C. for 4 hours, then spin-coated an additional 2-3 times and incubated at 37° C. overnight.

FIGS. 1A, 2A and 2B illustrate polyacrylate-fiber devices. The clear glassy look of the devices results from the polyacrylate coating, which whitens with hydration. The ability to utilize multiple fibers in the manufacturing process allows for precise engineering of the device to fit the specific needs of each target biomedical application. Coating of the device with emulsion embeds the fibers within the solid polyacrylate film and the film extends over the free space of the fiber mesh and gives the device reversible elasticity as well as prevents fluid leakage through the device (the device can absorb water).

Mechanical analysis has verified reversible elasticity of the devices, which increases with hydration. When under strain, the fibers within the device align and the device can stretch to an extent, yet when the strain is removed, the device returns to its original state without damage to the device establishing memory for the devices. A multi-fiber device (e.g., a 7-fiber yarn) results in a much stronger and thicker device (FIG. 2A) than the single fiber device shown in FIG. 1A without loss of elasticity as proved by mechanical analysis. Also, mechanical analysis has established that a multi-fiber cable is much stronger than a single fiber in terms of tensile strength, therefore, the resulting device will be more durable (e.g., have a much larger tensile strength and require a higher maximum force for failure). The multi-fiber devices appear to be most suited for deep tissue hernia patches and large vascular replacements such as aortic replacements because there is less area for leakage and the increased strength can extend the lifetime of the device once implanted. A prototype single fiber device was made having an 80 mm long device while a prototype multi-fiber device had a length of 20 mm. The prototypes were made using the lathe system shown in FIGS. 3A and 3B. The process includes application of fiber(s) to the Teflon® rod (support member 20) with continuous emulsion application, coating of device with emulsion, and drying of coating. The time between passes of lathe was altered between the two devices to yield an 80 mm long single fiber device (FIG. 2B) and a 20 mm long multi-fiber device (e.g., 7 fiber device) (FIG. 2A). In addition, the time spent at the end portions of the device (and other locations as appropriate) can control the thickness of the end rings to keep them consistent between devices or device types to comply with quality and regulatory standards.

The dimensions of the prototype devices have been varied by altering the time required during each pass of the lathe and the diameter of the Teflon® rod used for making the device. The computer program used for operating the lathe permits altering of the time needed per pass, which allows the system to produce relatively short (20-30 mm) fiber devices or relatively long (80 mm) fiber devices. The total time for manufacturing can also be varied so that the thickness of the devices can be controlled. Typically, the multi-fiber devices are wound for a shorter period of time than the single fiber devices. Devices ranging from about 1 mm to about 12 mm inner diameter have been made.

The dimensions of the device can be adjusted to fit the needs of the medical field. A small diameter Teflon® rod can be used for manufacturing devices for use in vein and artery replacements, while larger Teflon® rods can be used to manufacture devices for aortic or large artery replacements and various shunts. The thickness of the device can be altered by extending the manufacturing time or by utilizing multiple fiber strands processed into a single cable or "yarn" for winding. This can allow both fiber and polyacrylate film to prevent leakage of any fluids from within or into the device in vivo.

Figures 12A, 12B:
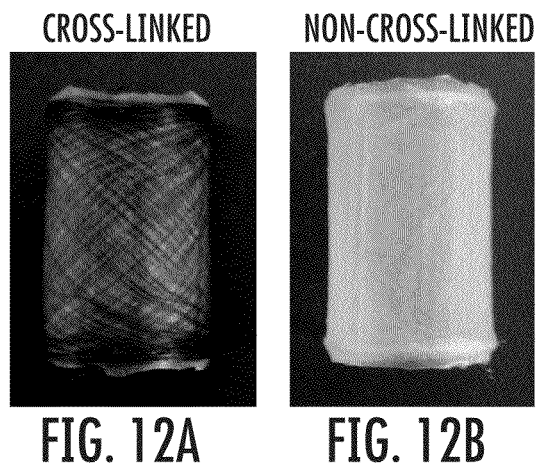
FIG. 12A is a digital photograph of a prototype medical construct made from NDGA-collagen fibers.
FIG. 12B is a digital photograph of a prototype medical construct made from non-cross linked fibers according to other embodiments of the present invention.

FIG. 12A is a photograph of a prototype device made from NDGA-collagen fibers and FIG. 12B is a photograph of a device with collagen fibers not cross-linked.

During production using non-NDGA crosslinked collagen fibers (FIG. 12B), the collagen fiber would swell into a gel and become weak. This caused some of the fiber to gel with the emulsion during application, forming a novel biocomposite material that forms a solid material easily during production without the need for excessive coating of the device with emulsion. These devices may be particularly suited for application to superficial and acute epidermal wounds and disturbances where high strength is not required.

Figure 13:
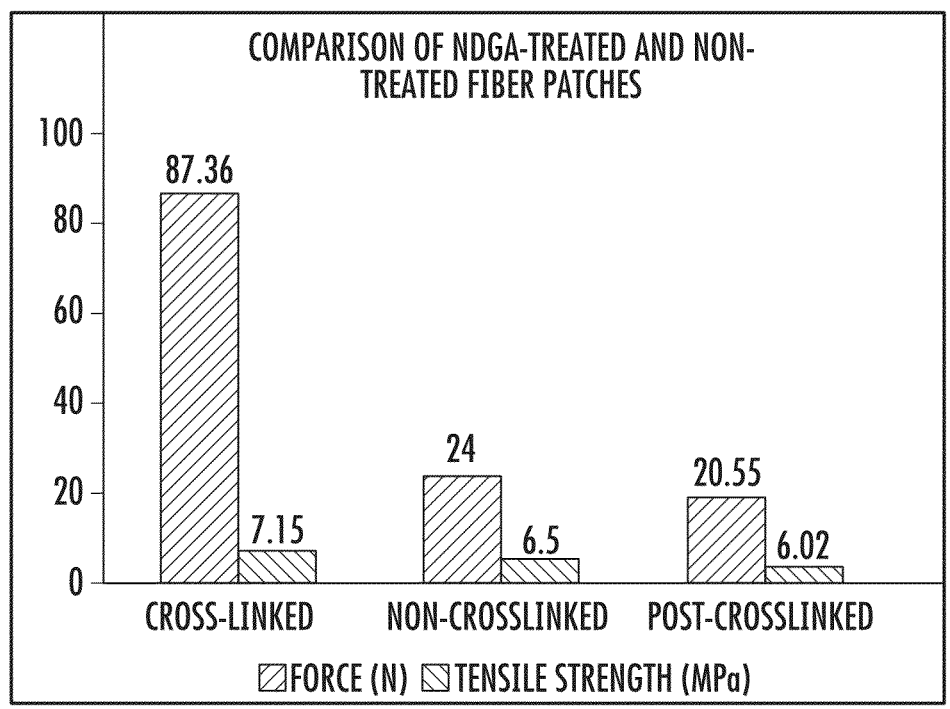
FIG. 13 is a bar graph of force (N) and tensile strength (MPa) for three different versions of collagen fibers: (a) NDGA-cross linked fibers; (b) non-cross linked fibers; and (c) collagen fibers that were cross-linked with NDGA after the winding process.

FIG. 13 shows that the non-crosslinked and post-crosslinked devices were much weaker than the ones formed from NDGA cross-linked collagen fibers in terms of maximum force required for failure, yet the tensile strength (normalized to the cross sectional area of the devices) was relatively equivalent. The non-crosslinked device yielded a softer material that felt more similar to the currently available wound care products than the NDGA-crosslinked devices; however, the strength of the device greatly decreases when the collagen is not crosslinked prior to application (winding or introduction onto the support member). Both cross-linked and non-crosslinked patches displayed memory upon hydration and mechanical analysis.

Mechanical Analysis of Manufactured Prototypes

The combination of NDGA-collagen fibers with a polyacrylate emulsion to form an elastic mesh device can be very beneficial to many biomedical applications, including artificial elastic tissue replacements. Mechanical analysis has verified that these materials possess reversible elasticity that increases with hydration. These devices can be considered "smart materials" since they can be manipulated to just below failure and, using memory, realign to their original confirmation without damage to the material. When under uniaxial strain, the polymer substrate allows the fibers to align within the device, at which point the device will not stretch any further. When the strain is removed, the device returns to its original relaxed state and the stress/relaxation cycle can be repeated, similar to what is observed for the majority of mammalian elastic tissues. In order to determine tensile strength, the devices were taken past this alignment stage with continuous force application to cause failure (see below). The prototype devices were mounted in 1000 lb load cell clamps and mechanical analysis was performed under uniaxial load after hydration for a minimum of 30 minutes in diH2O (deionized water).

Figure 16:
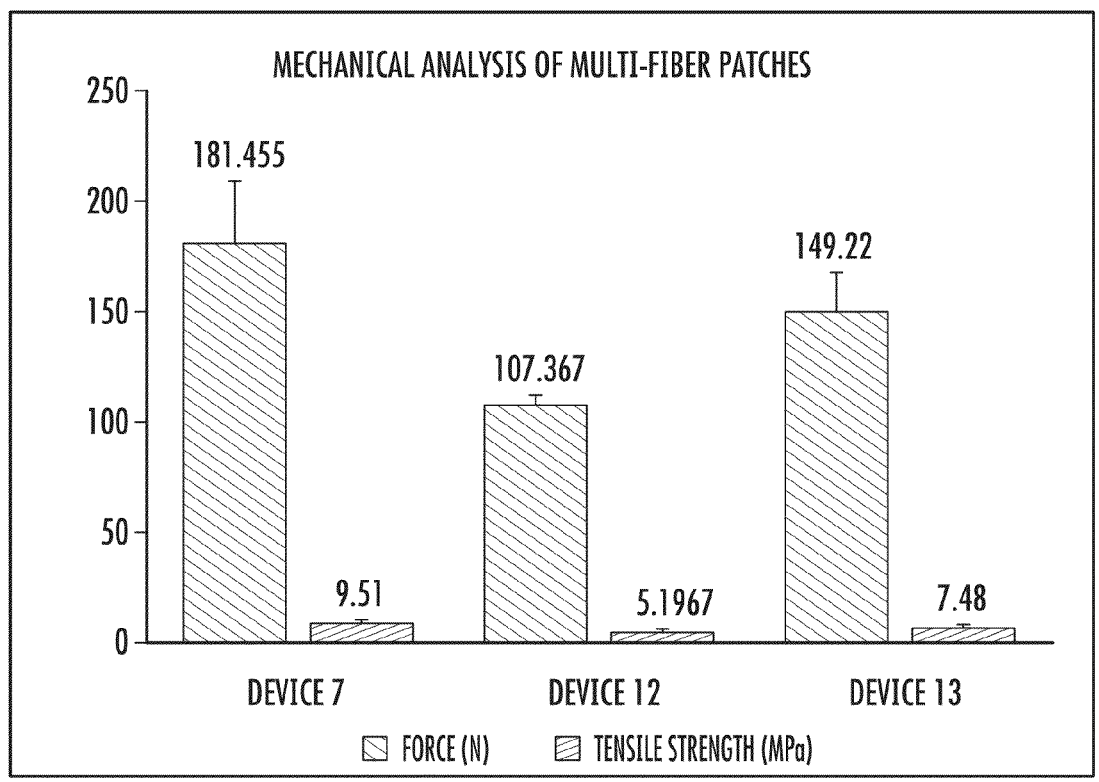
FIG. 16 is a bar graph of force (N) and tensile strength (MPa) for three different prototypes according to embodiments of the present invention.
Figure 17A:
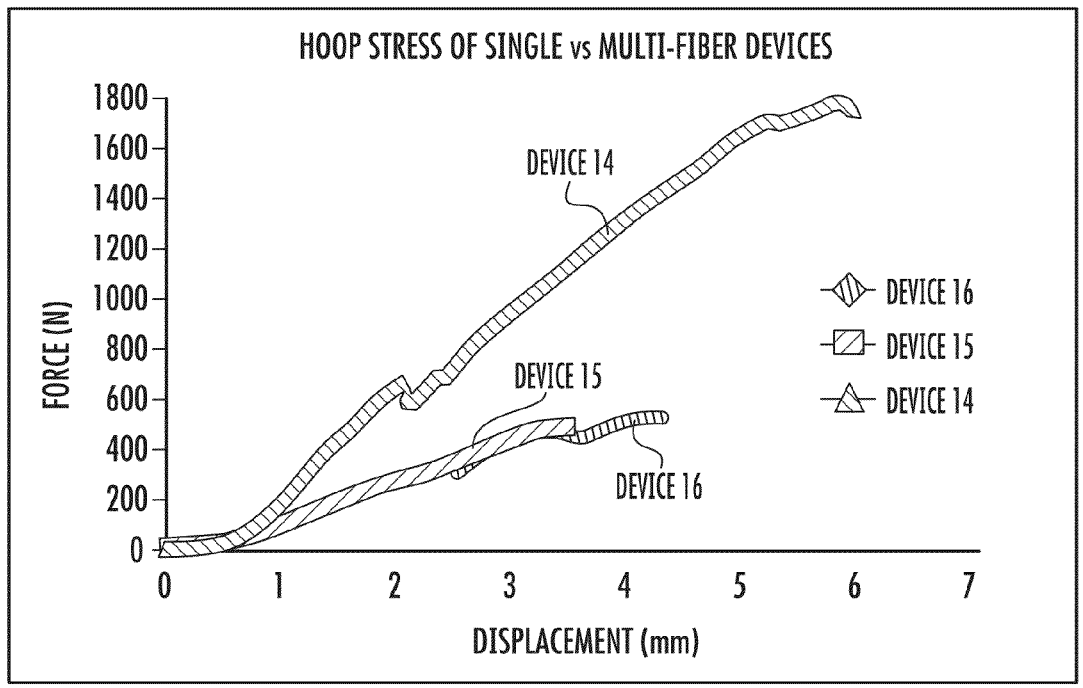
FIG. 17A is a graph of hoop stress, force (N) versus displacement (mm), for three different prototypes (two single fiber and one multi-fiber device) according to embodiments of the present invention.
Figure 17B:
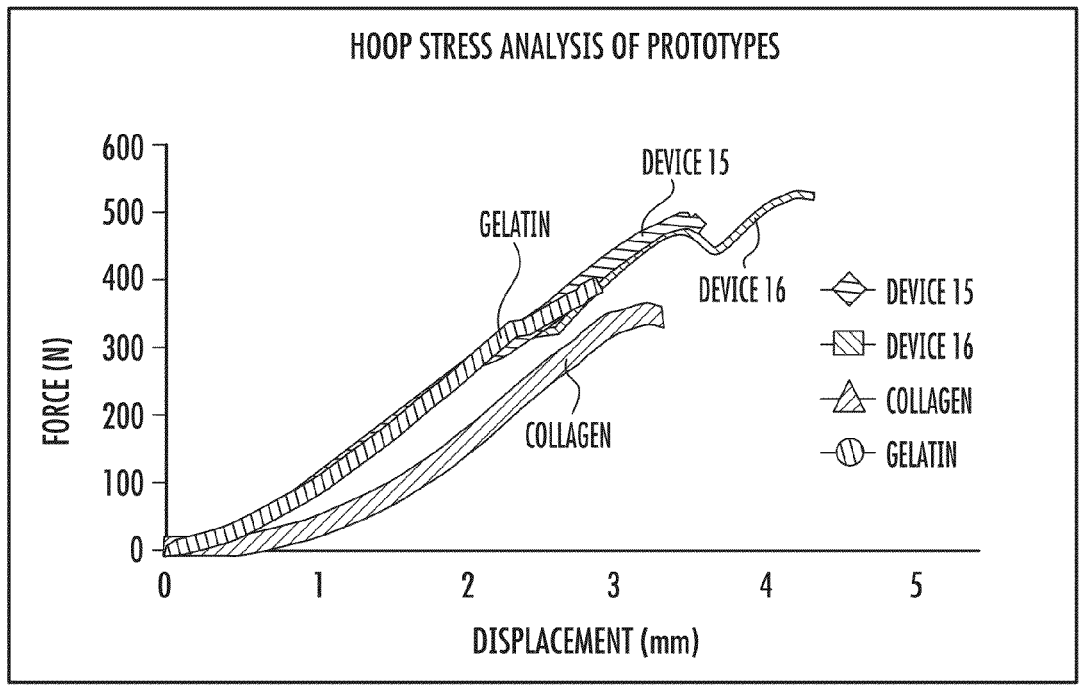
FIG. 17B is a graph of hoop stress analysis of force (N) versus displacement (mm), for collagen and gelatin and different prototypes according to embodiments of the present invention.

FIG. 14A illustrates a device (prototype 5) that was cut in a lengthwise direction and hydrated. FIG. 14B illustrates a relaxed fiber states and FIG. 14C illustrates the fibers align to the relaxed state. The devices were cut laterally along the device line then folded in half prior to placement in the load cell clamps as shown in FIGS. 14A, 14B. The cutting of the prototype device was to allow for removal of the device from the support member, before the Teflon® insert had been engineered that allows the devices to be removed from the rod without cutting. The prototypes no longer require cutting to remove and the devices can be analyzed in their intact cylindrical form, and this "intact" data is shown for the multi-fiber devices below (FIGS. 16, 17A, 17B). For prototypes/devices 1-6, different polyacrylate emulsion solutions were employed during the winding operation. Each emulsion used creates a polymer film with different physical and mechanical properties as shown in FIG. 15.

FIG. 15 illustrates the results of a mechanical analysis of 30 mm single fiber devices manufactured using different polyacrylate emulsions. As shown in FIG. 15, the strongest device formed (Device 4) used an emulsion synthesized from ethyl acrylate and methyl methacrylate in a 4:1 ratio respectively. This emulsion produces the strongest polymer films of all the emulsions synthesized and analyzed by the investigators. Device 1 and 2 both contained the same polyacrylate emulsion of butyl acrylate and styrene (7:3 ratio), but for device 2 the emulsion was mixed in a 1:1 ratio of emulsion to soluble collagen suspension (3%) prior to device production. By mixing the emulsion with soluble collagen, the amount of solid polymer added to the device was reduced, which appears to have caused the overall tensile strength and maximum force of the device to decrease. Also, the elasticity of this device was greatly diminished from other devices analyzed due to the decrease in polymer present in the device. Devices 5 and 6 were formulated using an emulsion that yields very weak films but possess the highest degree of elasticity of all the films (8:2 butyl acrylate to styrene). These devices were therefore not as stiff as the other devices, but possessed high maximum strain and deformation values and were highly elastic.

Mechanical analysis of the multi-fiber devices proved to be difficult due to the exponential increase in strength for these devices, especially when the devices were analyzed without lateral sectioning of the device prior to testing. During uniaxial mechanical analysis, devices would slip out of the clamps yielding a false maximum force as the devices never reached failure. This allowed re-testing of the devices multiple times since little damage was done to the devices during testing and the testing produced an average tensile strength and maximum force for the devices. An average of three tests were performed per device in an attempt to achieve an accurate tensile strength. Four devices were manufactured: Device 7, 12, 13, and 14. Devices 7 and 14 were manufactured using a 7:3 ratio emulsion of butyl acrylate to styrene. Devices 12 and 13 were both manufactured using a 4:1 ratio emulsion of ethyl acrylate to methyl methacrylate. Device 7 was manufactured using the standard device program with 20 minutes total production time where the lathe spent 5 seconds between passes at the ends of the device. However, for devices 12-14, the time spent between passes where the end rings are wound was minimized after 10 minutes of production in order to reduce the thickness of the end rings for these devices. The time spent at the ends of the devices were 5 seconds initially and was reduced to 2 seconds for the remaining 10 minutes of production for devices 12-14. This reduction in time yielded a more even-distribution of fiber within the devices and reduced the bulkiness of the devices at the ends.

As shown in FIG. 16, the maximum force obtained for each device was significantly greater than was observed for the single fiber devices (shown in FIG. 15), yet the tensile strength was relatively equal. This is most likely due to the increased thickness of the multi-fiber devices (e.g., 7 fibers) factoring into the overall tensile strength calculated from the cross-sectional area of the device. However, the area of the devices drastically decreases during the tensile test due to the fiber alignment within the device, therefore the calculated tensile strength for device presented here are relative only to the initial cross sectional area and the true tensile strengths are likely significantly greater than what is presented here.

Tensile strength was also determined for the devices by removing them from the Teflon® rod support member without lateral cutting, leaving the device in an intact cylinder and putting uniaxial tension on the device from the inside. It is believed that this test provides the most accurate data achievable under uniaxial mechanical analysis since the device is not able to slip from the clamps. It is currently contemplated that the tensile tests for analyzing the prototype devices will utilize this method of testing. Burst test data for cylindrical devices maxed out at about 75 psi (to burst using pressurized air from the inside) for fully coated devices.

Tensile data for devices formed with various natural (collagen) and synthetic (polyacrylate) materials are shown in FIGS. 17A and 17B. Devices 15 and 16 were single fiber devices manufactured using butyl acrylate and methyl methacrylate. Device 14 was a 7-fiber device manufactured using a butyl acrylate and styrene emulsion.

FIG. 17A compares the mechanical properties of the single and multi-fiber devices. Analysis demonstrated a maximum force of approximately 1770 N for the seven fiber device (Device 14) as opposed to approximately 500 N maximum force for the single fiber devices (Devices 15, 16). This data provided here is believed to be the most accurate and depicts a higher load capacity than was observed for these same patches in the basic uniaxial tensile tests that utilize a clamping method (FIGS. 15, 16). The seven fiber device (Device 14) was over three times stronger than the single fiber ones (Devices 15, 16), which was an expected result for these highly reinforced devices. The maximum displacement for the seven fiber device (Device 14) was also greater than was observed for the single fiber ones (Devices 15, 16). The data shows that the elasticity appears to have increased for these devices, indicating retention of elasticity in the multi-fiber devices which appears to have increased concurrently with the increase in strength.

The data presented in FIG. 17B shows that gelatin-fiber devices and the polyacrylate devices were very similar in terms of mechanical behavior, where both devices followed the same force/displacement trend. However, during initial testing, the gelatin devices did not reach as high of a maximum force or displacement as the polyacrylate devices achieved. Incorporation of the polyacrylate film allowed the device to stretch until the mechanical strength of the fibers within the device was tested. The polyacrylate film and collagen fibers, which may include NDGA treated collagen fibers, can act to enhance the mechanical properties of the material.

In addition to the tubular device structures discussed above, thus far, over 20 different patches have been manufactured using this new technique that combines collagen fibers with various water-based polyacrylate emulsions synthesized through microemulsion polymerization. Again, these emulsions have the ability to be synthesized in a one-step process and can include covalently bound antibiotics that may be incorporated into the patches for additional utility. The patches were manufactured using a mechanical Sherline lathe.

Some prototypes were made by winding a single 30 m-70 m long fiber onto a Teflon® sheet (FIG. 3C) with substantially continuous application of a polyacrylate emulsion. The application was by hand or manual but automated devices to apply the emulsions may be used. Substantially continuous addition of the emulsion provides a sticky adhesive for the fibers to adhere to the Teflon® sheet and remain where set on the sheet and also provides a water proof coating for the fiber that inhibits or prevents swelling and subsequent deformation of the device upon hydration. After the fiber has been wound for 20-60 minutes, depending on the size and thickness desired, the mesh fabric is spin coated 2-3 times with the emulsion, incubated at 37° C. for 4 hours, then coated an additional 2-3 times and incubated at 37° C. overnight. This procedure produces a solid polyacrylate film in the interstitial space between fibers and also a polymer film coating the surface of the fiber mesh which gives the patch the reversible elasticity desirable for application to wound beds and other elastic tissues.

Figure 19A:
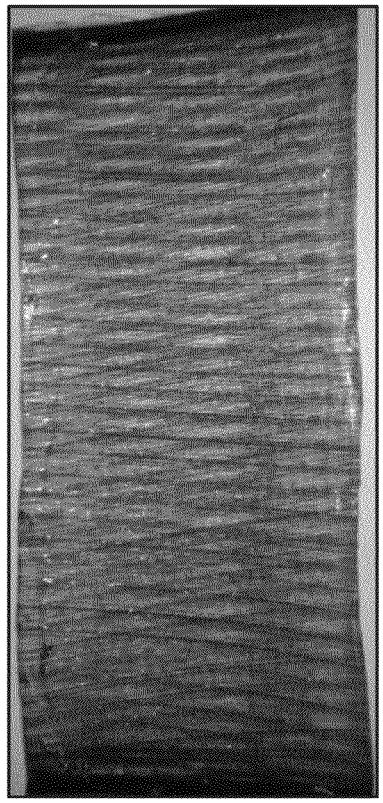
FIGS. 19A-19C are digital photographs of single fiber patches having different fiber angles according to embodiments of the present invention.
Figure 19B:
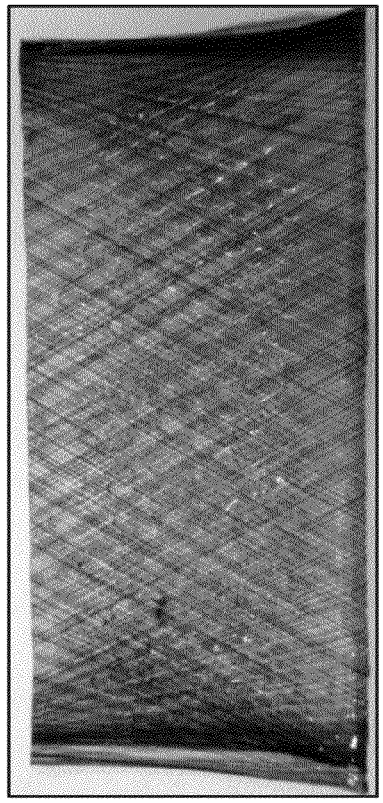
Figure 19C:
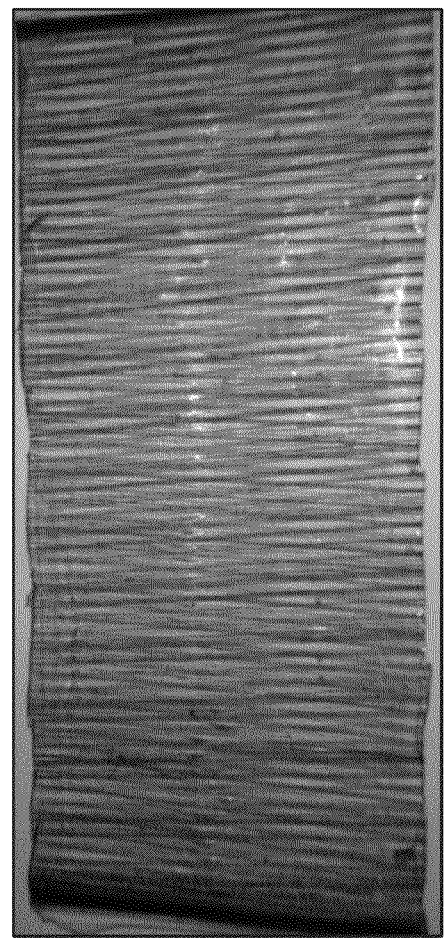
Figure 23B:
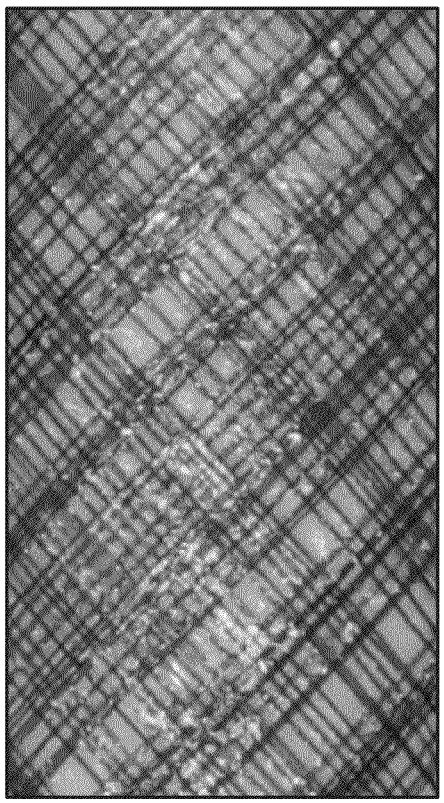
FIGS. 23A-23D are enlarged digital photographs of cylindrical biomaterials with different fiber angles and/or numbers of fibers.
Figure 23D:
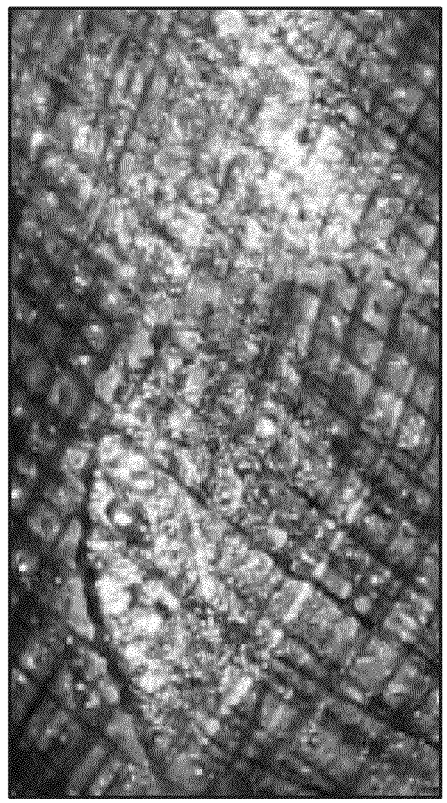
Figure 23A:
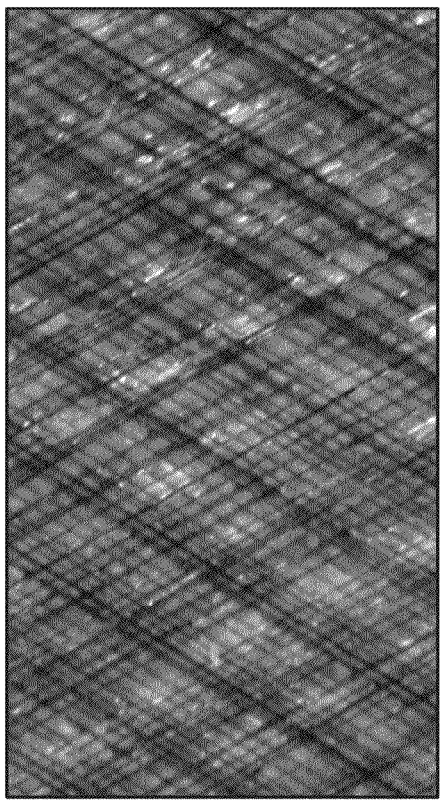
Figure 23C:
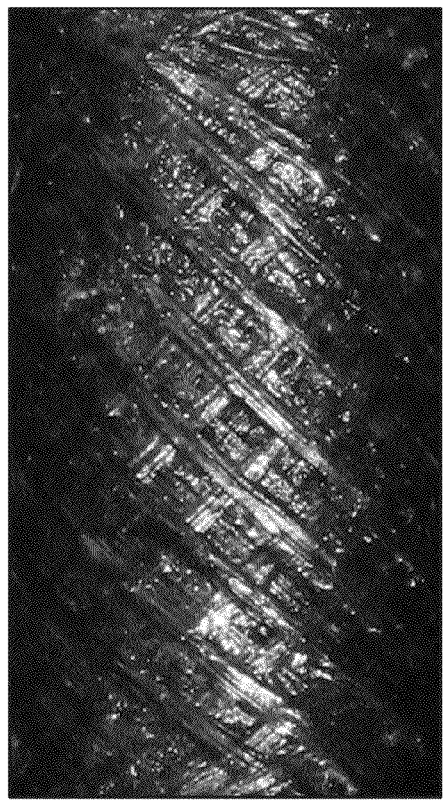

FIGS. 19A-19C show examples of single fiber (80 mm long) patches with varying fiber angles. FIG. 19A shows a patch fiber angle of 25°. FIG. 19B shows a patch with a fiber angle of 15° and FIG. 19C shows a patch with a fiber angle of 5°. FIGS. 22A-22D also illustrate varying fiber angles using NDGA cross-linked collagen fiber-polyacrylate biomaterial to form substantially flat patches. FIGS. 23A-23D illustrates cylindrical biomaterials with NDGA cross-linked collagen fiber-polyacrylate biomaterials (FIG. 23C illustrates a 7 fiber biomaterial and FIG. 23D illustrates a single fiber material).

Figure 18A:
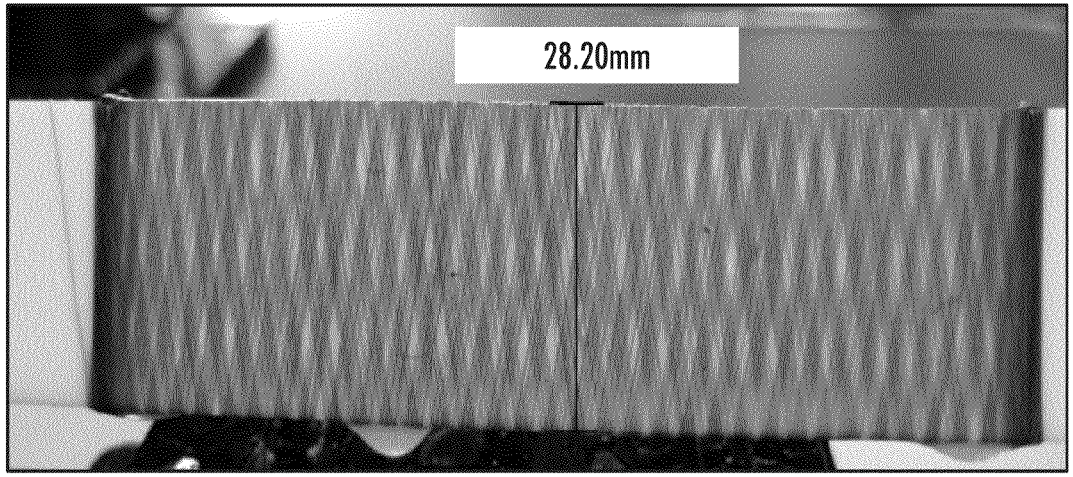
FIG. 18A is a digital photograph of a flat polyacrylate fiber patch according to embodiments of the present invention.
Figure 18B:
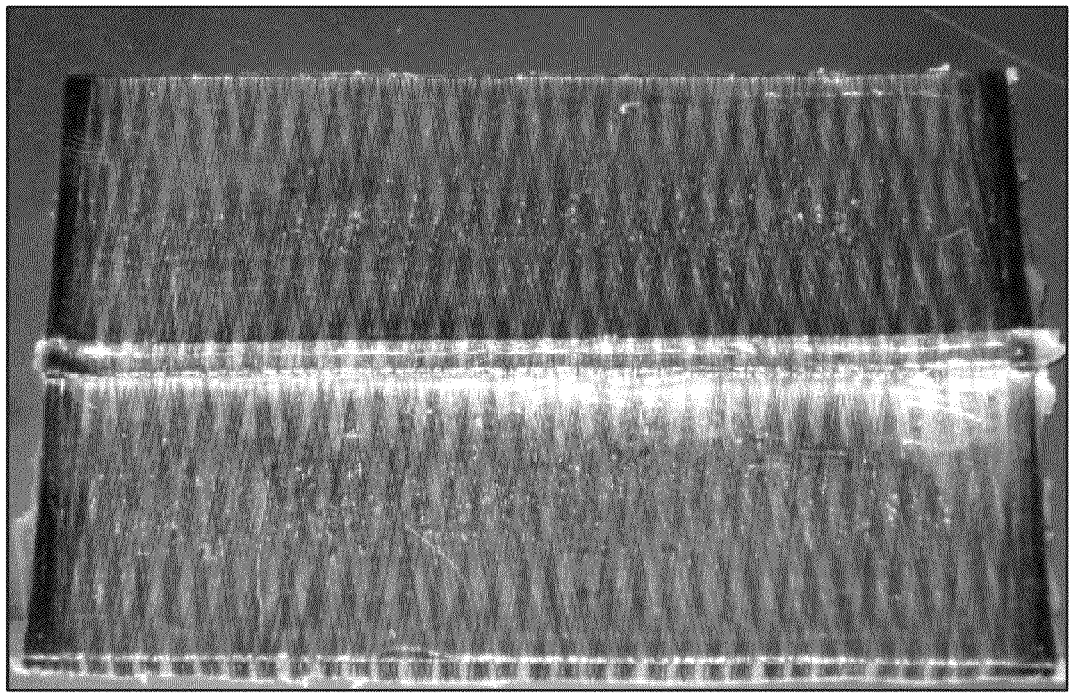
FIG. 18B is a digital photograph of the patch shown in FIG. 18A that has been cut into two individual patches according to embodiments of the present invention.
Figure 20A:
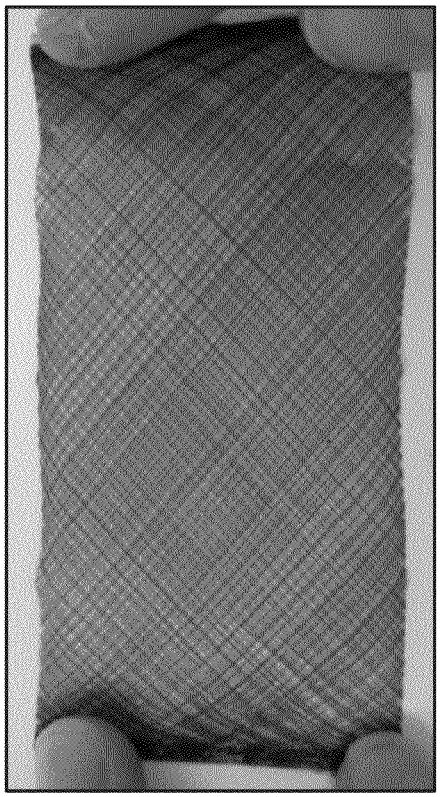
FIG. 20A is a digital photograph of a single fiber patch in a pre-hydration state according to embodiments of the present invention.
Figure 20B:
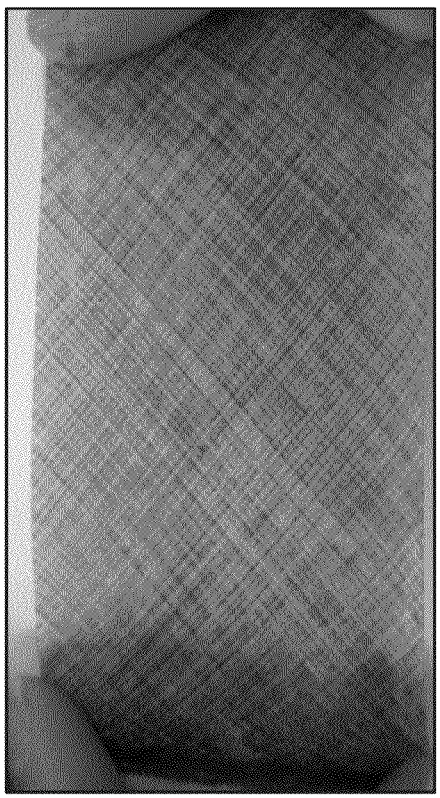
FIG. 20B is a digital photograph of the single fiber patch shown in FIG. 20A in a post-hydration state according to embodiments of the present invention.

The prototypes were made using a Teflon® sheet and lathe (see, e.g., FIG. 3C). The finished patch is then removed from the Teflon® sheet, typically by cutting the fiber mesh laterally from end to end, revealing a solid substantially rectangular fabric that can then be packaged and sold in this form, substantially "as-is" (FIGS. 20A, 20B). The reinforced ends of the patch are approximately three times stronger than the interior of the patch, making this area ideal for suturing of the device in a wound or chronic ulcer bed or for application as a surgical mesh (FIGS. 19A-C) and also prevent unraveling or fraying of the fibers in the patch. The shape of the Teflon® sheet can also be adjusted so that two rectangular patches are fabricated from a single manufacturing process (FIGS. 18A, 18B). This provides double the manufacturing capability without increasing the amount of fiber needed. Or, for instances where a double layer patch is required (such as for deep chronic wound treatment), the patch can be removed from the Teflon® sheet without cutting and the single device can be sutured into the wound bed.

FIGS. 18A and 18B illustrate flat polyacrylate-collagen fiber biomaterial patches. In the example shown, the patch is cut along the length of the Teflon® and peeled off to reveal a single patch that can then be cut into two or more individual patches. When the (rectangular) patches are held by the reinforced end rings and pulled away from one another, the patches display properties similar to that of a fiber-free polyacrylate film, namely it exhibits memory after deformation. However, when the cut ends of the patch are held and pulled away from one another the patch acts as a true fiber-reinforced composite where the fibers provide intense strength and little elasticity is observed at low amounts of strain.

The dimensions of the patches can vary. A smaller area Teflon® sheet can be used for manufacturing smaller patches while larger Teflon® sheets can be used to produce larger patches to cover larger surfaces, such as high total body surface areas. The thickness of the patch can be varied by extending the manufacturing time or by utilizing multiple fiber strands processed into a single cable for application or by using other multi-fiber devices, including multi-fiber cables and braids that can then be manufactured into patches.

A multi-fiber cable using strands that are loosely wound into a cable then applied to the rod for a patch results in a much stronger and thicker patch. It is also contemplated that the multiple fibers can be wound concurrently but separately. Also, mechanical analysis has established that a multi-fiber cable (e.g., 7 fiber) is stronger (e.g., 2-3 times stronger) than a single fiber in terms of tensile strength, therefore, when a cable is used for patch production, the resulting patch should be more durable.

Under standard manufacturing conditions, the internal surface of the patch typically has only polyacrylate-coated collagen fibers whereas the external surface of the patch is coated with extra layers of polyacrylate emulsion to provide a polymer-based barrier to inhibit or prevent bacterial translocation into the wound bed. However, this feature can easily be modified to fit the specific needs of the wound bed where either or both surfaces (external or internal) can be coated with emulsion post-production sealing the collagen fibers within the patch and preventing fiber interaction with the surrounding tissue/fluid. The polyacrylate portion of the patches appears to absorb aqueous media (FIGS. 20A, 20B), making this formulation appropriate for application to wound beds with high exudates. By controlling the amount of polymer in the patch composition, the dressing or covering can be manufactured to fit the needs of highly exudating wound beds by coating both surfaces of the patch.

FIGS. 20A and 20B illustrate a single collagen fiber patch coated with polyacrylate emulsion. Upon absorption of aqueous media, the polymer transforms from translucent (FIG. 20A) to solid white (FIG. 20B) in the interstitial space between fiber and on the surface of the patch.

Figure 21:
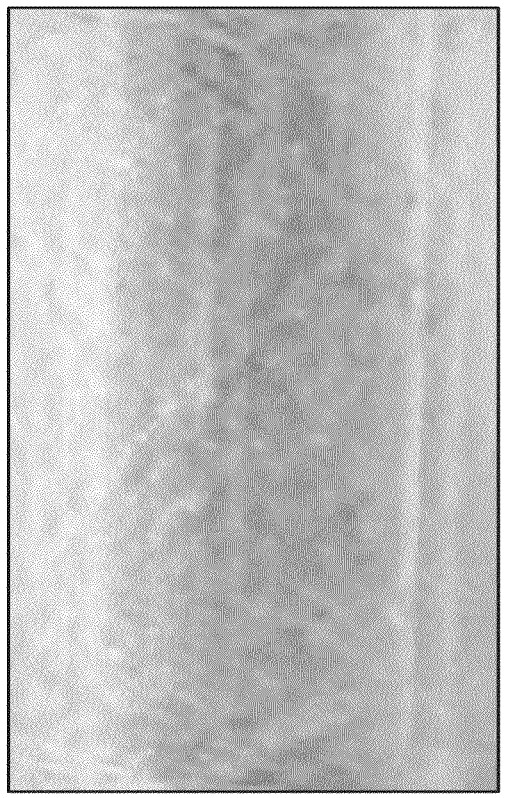
FIG. 21 is a digital photograph of an un-crosslinked fiber-polyacrylate biomaterial according to some embodiments of the present invention.
Figure 22B:
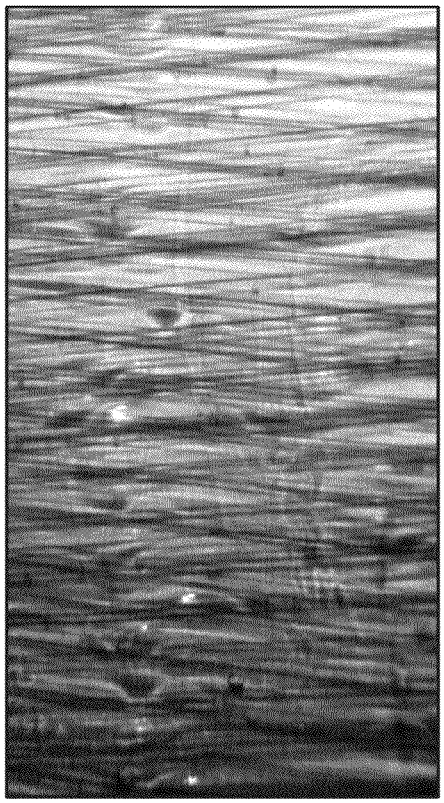
FIGS. 22A-22D are enlarged digital photographs of flat rectangular biomaterial with different fiber angles according to some embodiments of the present invention.
Figure 22D:
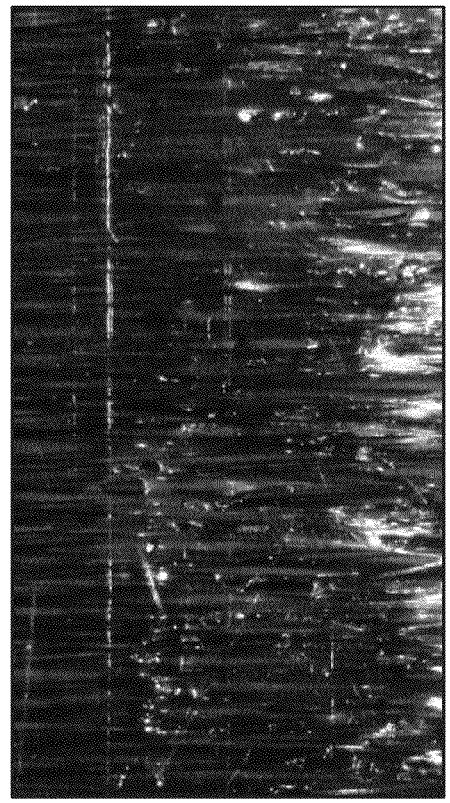
Figure 22A:
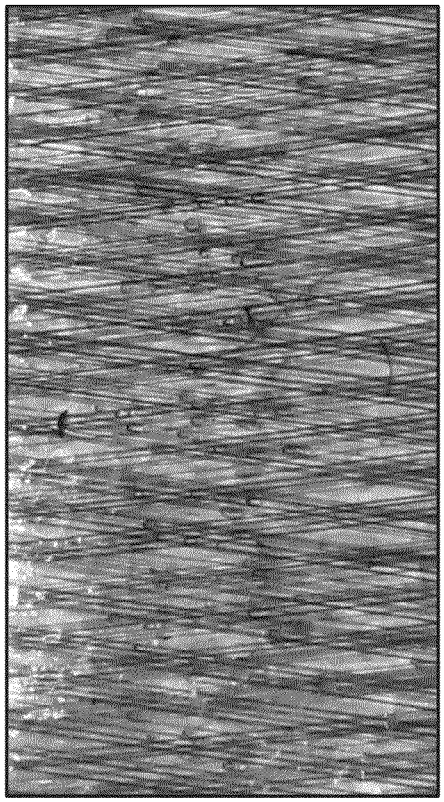
Figure 22C:
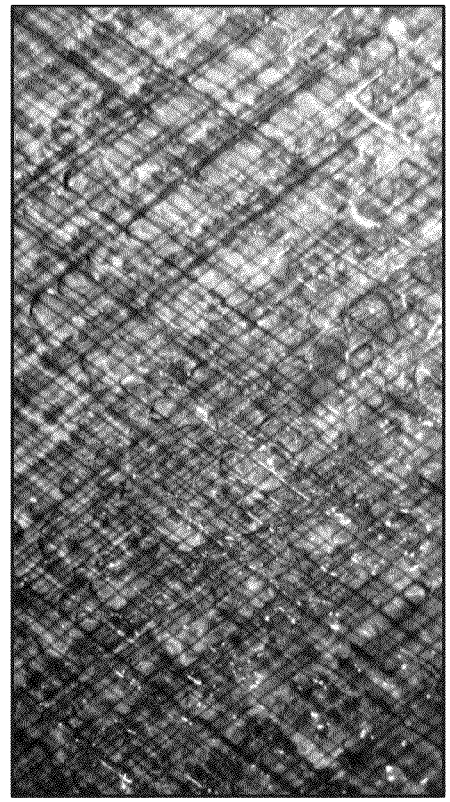

Patches using NDGA crosslinked collagen fibers has also been explored as shown in FIG. 21. During manufacturing, the un-crosslinked collagen fiber would swell into a gel and become weak, which caused some of the fiber to gel with the emulsion during application forming a novel biocomposite material. After the collagen fiber patch was formed, the fibers were attempted to be cross-linked with NDGA prior to final coating of the patch with emulsion. The post-production crosslinking was unsuccessful since the polyacrylate film that coats the fibers during manufacturing prevented NDGA interaction with the collagen. The non-crosslinked and post-crosslinked patches were weaker than the ones formed from NDGA-collagen fibers in terms of maximum force required for failure, yet the tensile strength (normalized to the cross sectional area of the patches) was relatively equivalent. Although the opaqueness of the non-crosslinked patch may be of utility to wound dressings where visibility of the wound bed is desired, the strength of the patch greatly decreases when the collagen is not crosslinked prior to application.

Mechanical Analysis of Manufactured Prototypes

The combination of NDGA-collagen fibers with a polyacrylate emulsion to form an elastic mesh material can be very beneficial to many biomedical applications, including topical wound dressings. Mechanical analysis has verified that these fabrics possess reversible elasticity that increases with hydration. These fabrics can be considered "smart materials" since they can be manipulated to just below failure and using memory realign to their original confirmation without damage to the material. When under uniaxial strain, the polymer substrate allows the fibers to align within the patch, at which point the patch will not stretch any further. When the strain is removed, the device returns to its original relaxed state and the stress/relaxation cycle can be repeated. In order to determine tensile strength, the patches were taken past this alignment stage with continuous force application to cause failure (see below). Patches were mounted in 1000 lb load cell clamps and mechanical analysis was performed under uniaxial load after hydration for a minimum of 30 minutes in diH2O.

Figure 24:
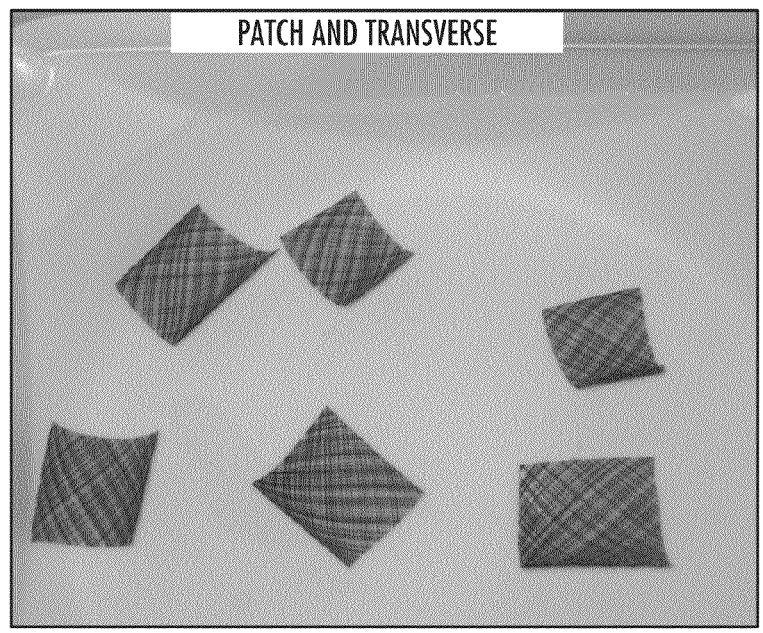
FIG. 24 is a digital photograph of a single patch that was cut into sections, some transverse (trans) to the fiber alignment according to embodiments of the present invention.

A single 80 mm long patch was cut into sections relative to the fiber alignment within the patch as shown for example, in FIG. 24. Six sections were cut transverse (trans) to the fiber alignment, and three sections were cut longitudinally (long). Also, the two reinforced end rings of the patch were sectioned and analyzed individually (ends). All sections were hydrated for 30 minutes in diH2O prior to mechanical analysis.

It was observed that regardless of the direction of sectioning (transverse or longitudinal), the wider the section of patch analyzed the greater the maximum force and tensile strength were for the section when the pitch angle is relatively high. However, for the reinforced end ring sections of patch, the tensile strength was an average of three times that of the internal sections due to the high maximum force observed for very narrow specimens. The stiffness of the parallel fiber ring at the terminal ends was much greater than for the internal portion of the patches, which caused a decrease in the amount of deformation and elasticity observed for the specimens but a drastic increase in tensile strength. For patches 8 and 9, the transverse sections were much wider than the longitudinal sections, which lead to the higher maximum force for these sections. However, other patches (data not shown) have exhibited higher maximum forces for the longitudinal sections which were wider than the transverse sections. Therefore, it is believed that fiber alignment does not materially affect (or affect at all) the tensile strength or maximum force observed for the patch sections and patch deformation in any direction should yield equivalent stiffness and strength.

Non-sectioned intact patches were also analyzed that were 30 mm in length. The patches were cut laterally along the patch line, then folded in half prior to placement in the load cell clamps (see above). The force of the intact patch was 3 times greater than that of the transverse/longitudinal sections cut from an 80 mm patch, and twice that of the reinforced end rings. This analysis is expected to be more representative of what the mechanical properties of the patch will be when applied to a wound bed or other applications where the entire patch is utilized un-sectioned.

Figure 25:
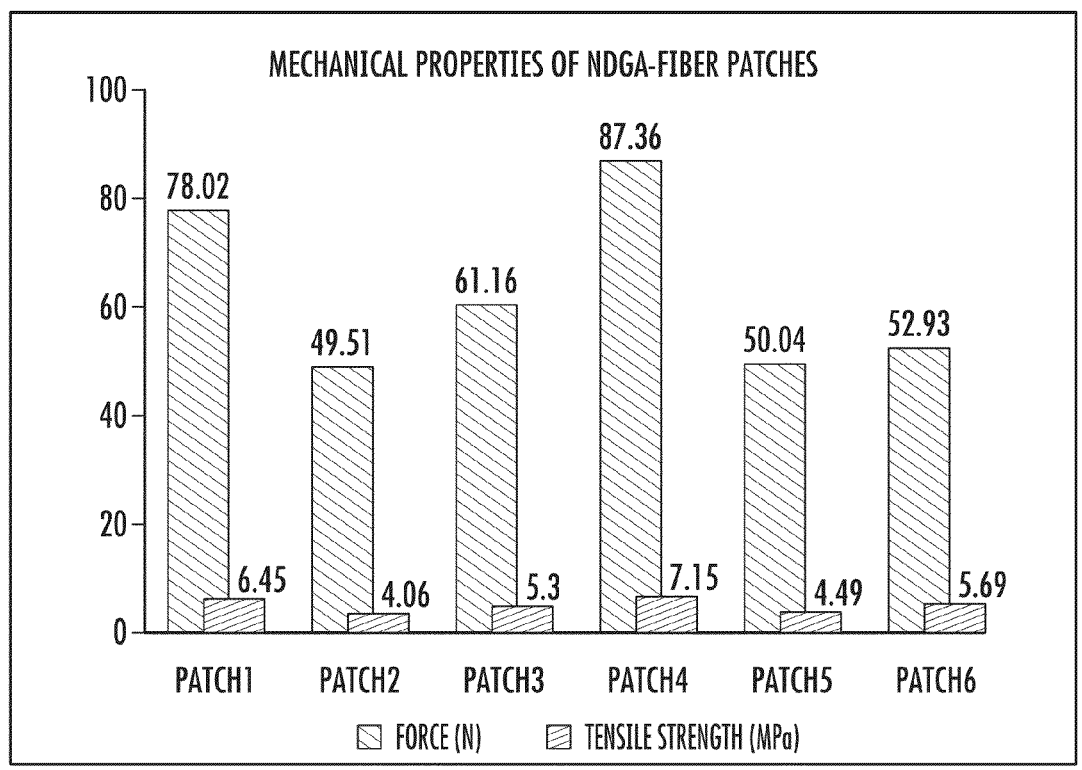
FIG. 25 is a bar graph of force (N) and tensile strength (MPa) for 6 different patches with six different polyacrylate emulsion solutions according to some embodiments of the present invention.
Figure 26:
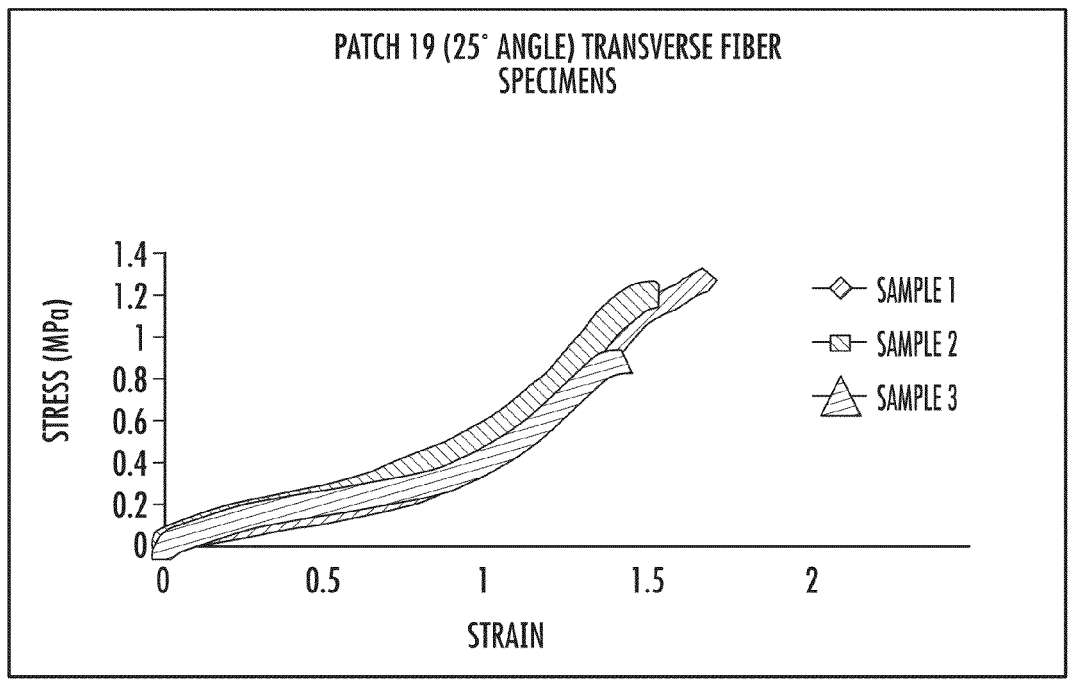
FIG. 26 is a graph of stress (MPa) versus strain for three different samples according to embodiments of the present invention.
Figure 27:
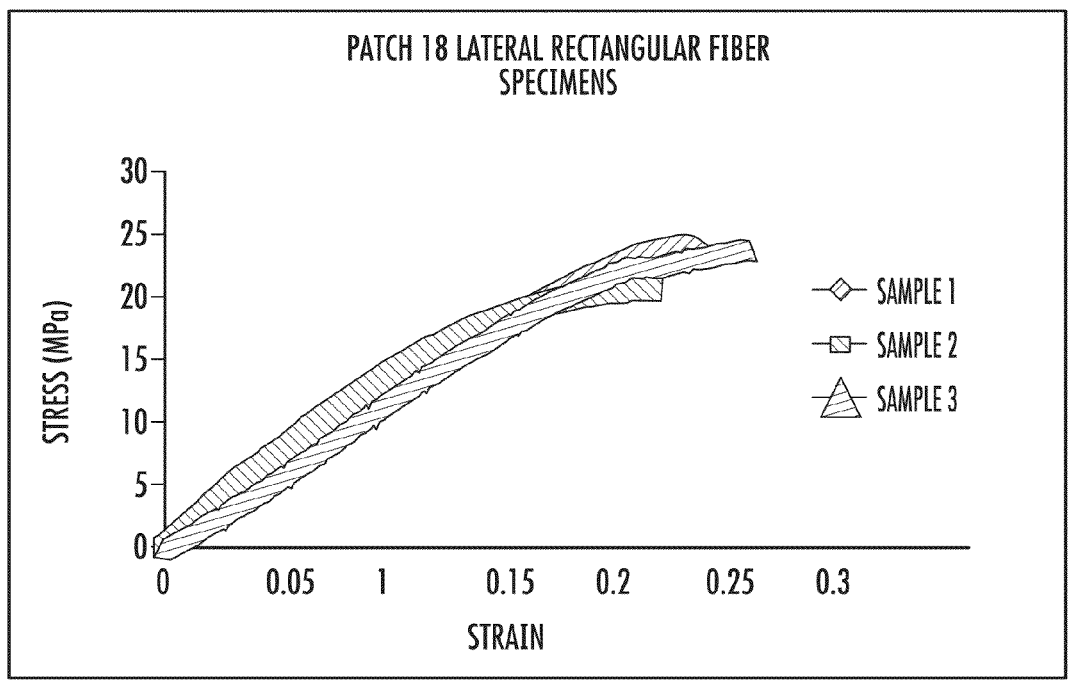
FIG. 27 is a graph of stress (MPa) versus strain for three different samples according to embodiments of the present invention.
Figure 28:
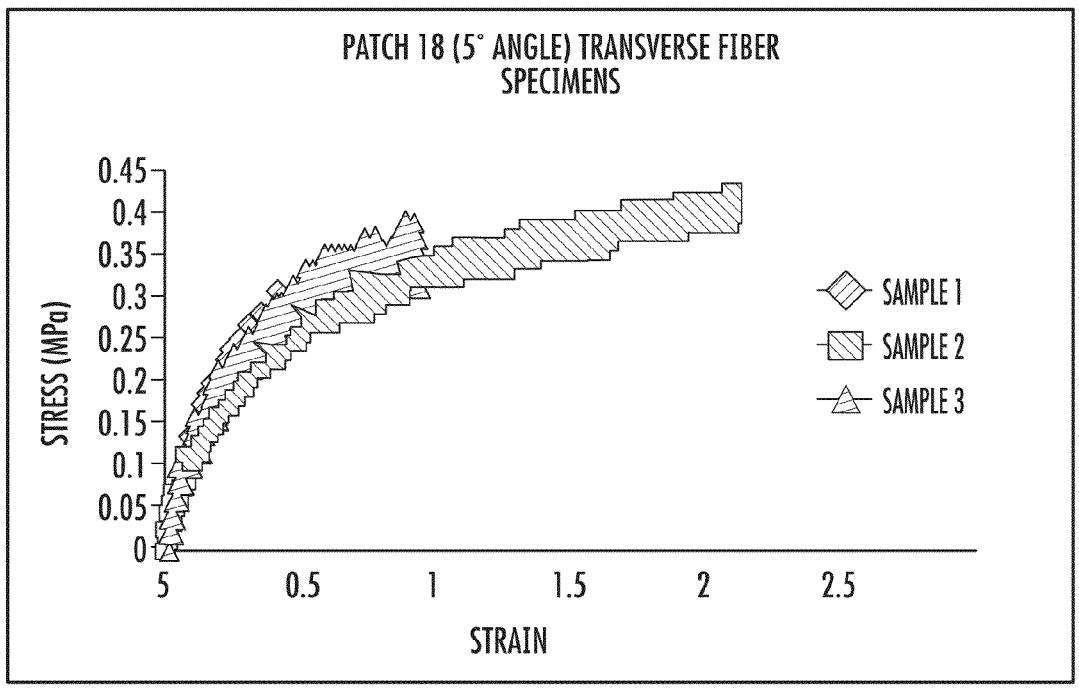
FIG. 28 is a graph of stress (MPa) versus strain for three different samples according to embodiments of the present invention.
Figure 29:
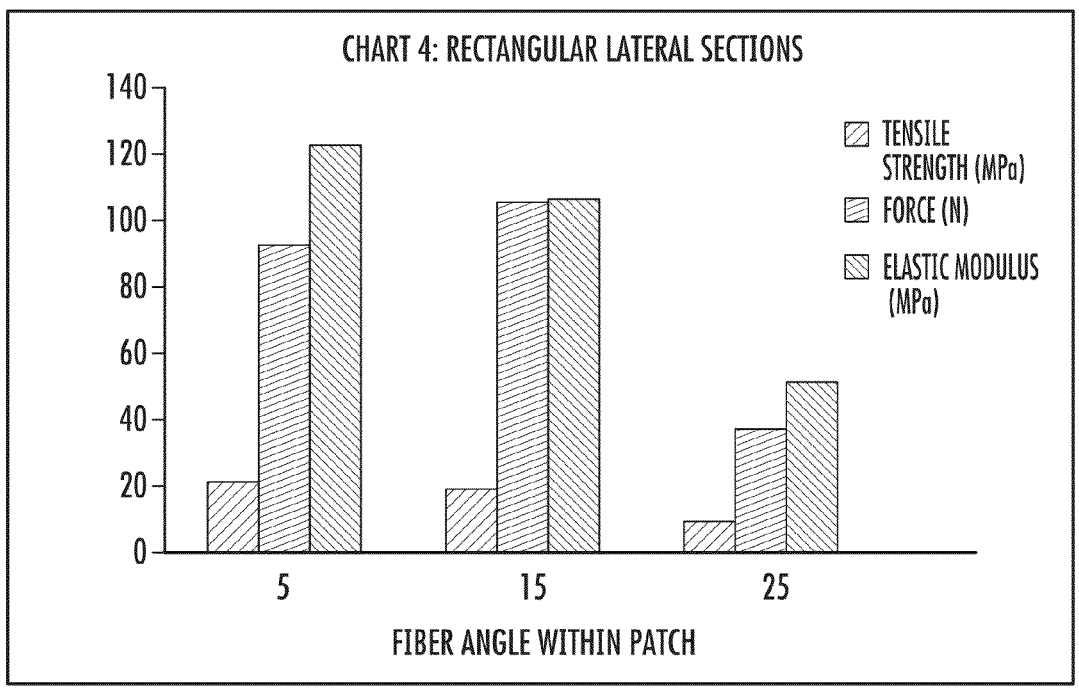
FIG. 29 is a bar graph of tensile strength (MPa), Force (N) and elastic modulus (MPa) for different fiber angles according to embodiments of the present invention.
Figure 30A:
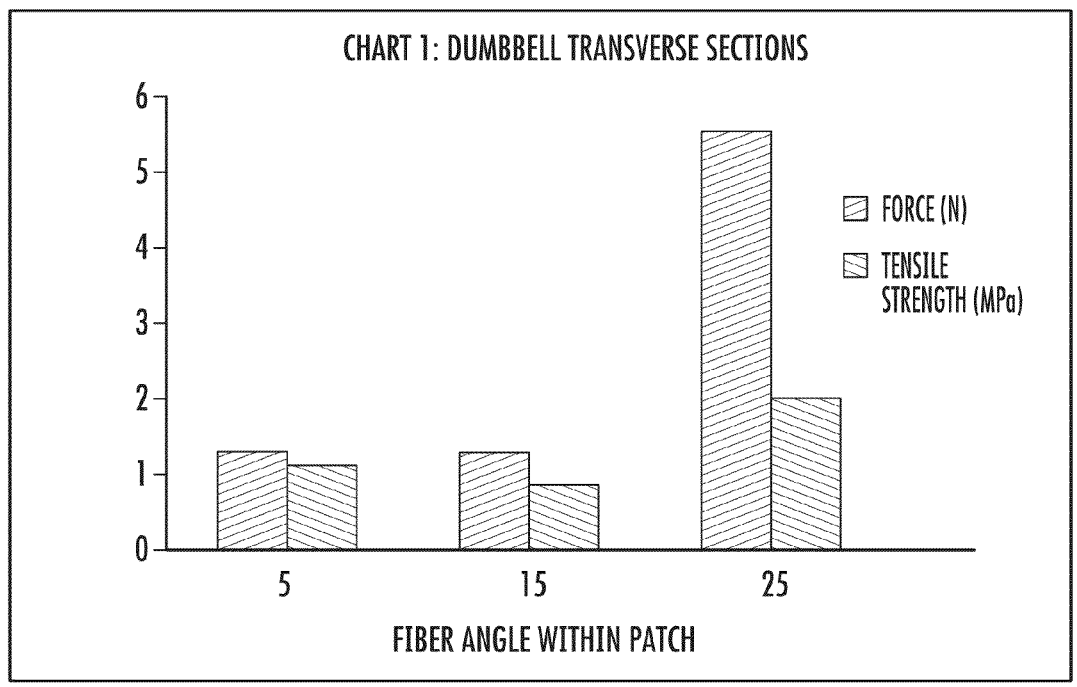
FIGS. 30A and 30B are bar graphs of force (N) and tensile strength (MPa) for different fiber angles in dumbbell transverse sections (FIG. 30A) and dumbbell lateral sections (FIG. 30B) according to embodiments of the present invention.
Figure 30B:
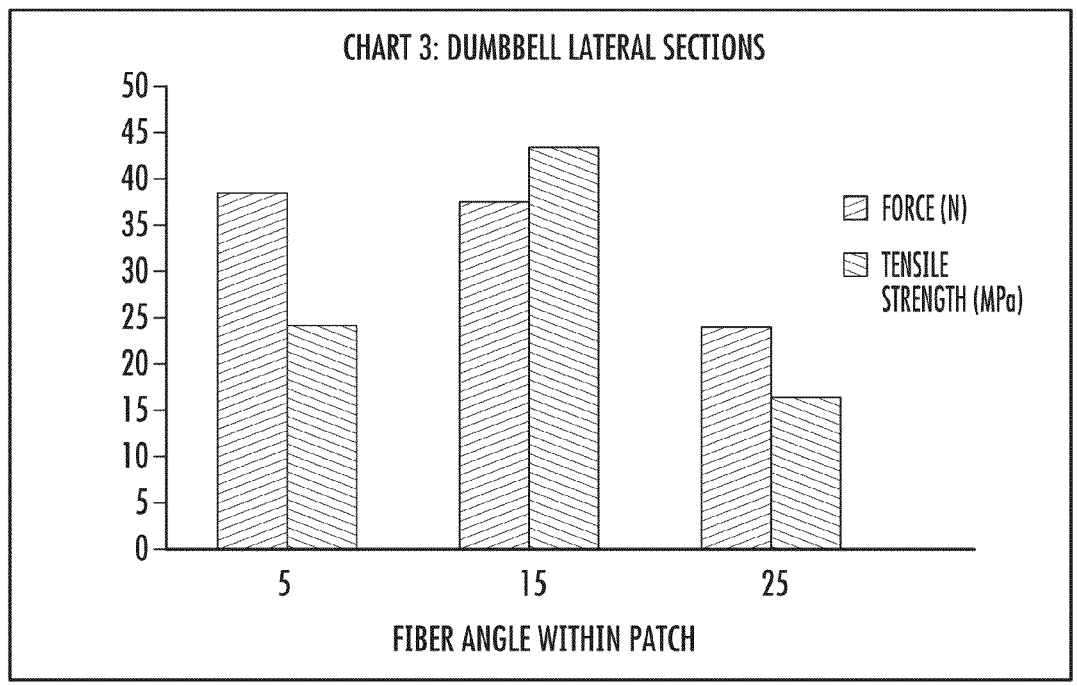
Figure 31A:
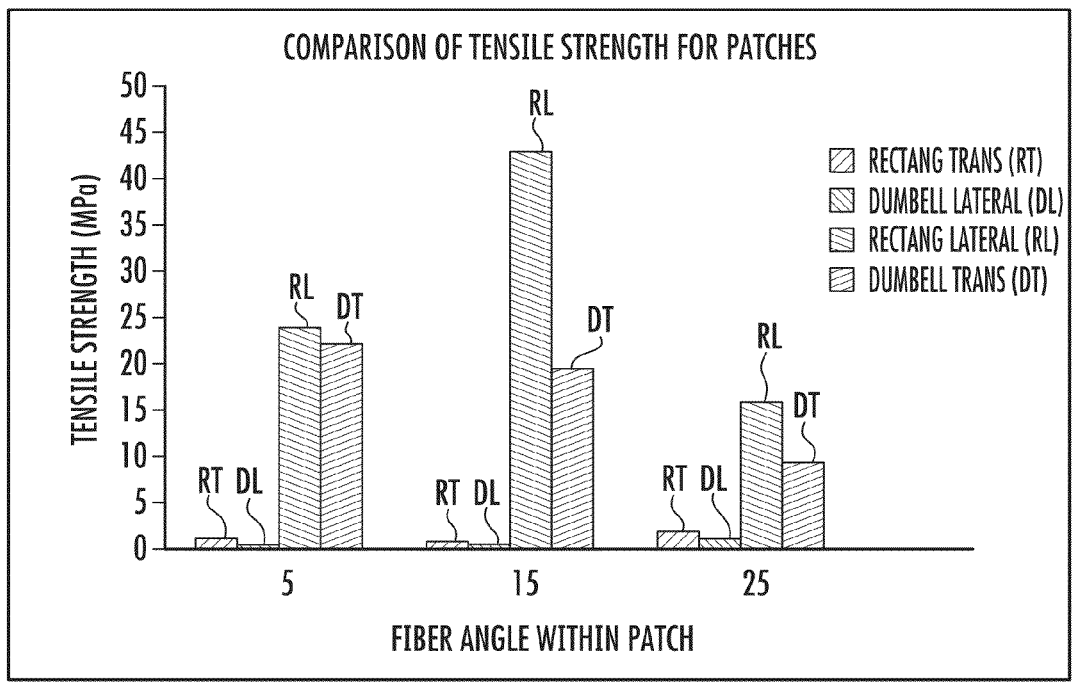
FIG. 31A is a bar graph of tensile strength (MPa) versus fiber angle for various samples according to embodiments of the present invention.
Figure 31B:
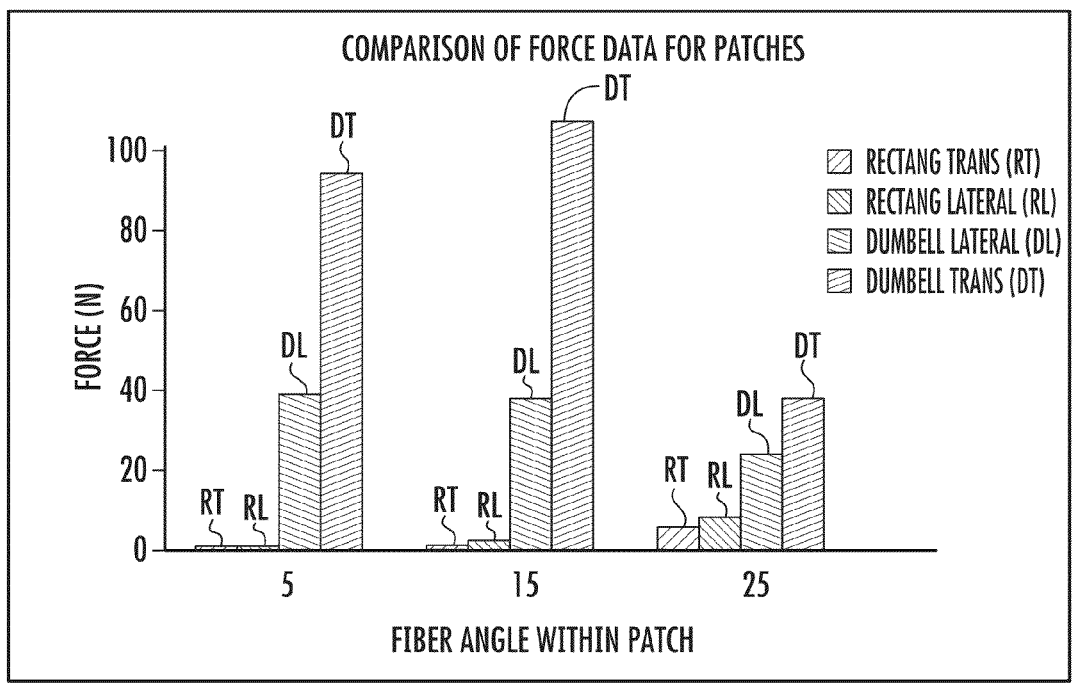
FIG. 31B is a bar graph of force (N) versus fiber angle for the various samples shown in FIG. 31A according to embodiments of the present invention.

For patches 1-6, different polyacrylate emulsion solutions were employed during the patch formation process, where each emulsion used creates a polymer film with different physical and mechanical properties as shown in FIG. 25. The strongest patch formed (Patch 4) used an emulsion synthesized from ethyl acrylate and methyl methacrylate in a 4:1 ratio respectively. This emulsion produces the strongest polymer films of all the emulsions synthesized and analyzed by the investigators. Patch 1 and 2 both contained the same polyacrylate emulsion of butyl acrylate and styrene (7:3 ratio), but for patch 2 the emulsion was mixed in a 1:1 ratio of emulsion to soluble collagen suspension (3%) prior to patch production. By mixing the emulsion with soluble collagen, the amount of solid polymer added to the patch was reduced, which appears to have caused the overall tensile strength and maximum force of the patch to decrease. Also, the elasticity of this patch was greatly diminished from other patches analyzed due to the decrease in polymer present in the patch. Patches 5 and 6 were formulated using an emulsion that yields very weak films but possess the highest degree of elasticity of all the films (8:2 butyl acrylate to styrene). These patches were therefore not as stiff as the other patches, but possessed high maximum strain and deformation values and were highly elastic.

Patches 17, 18, and 19 are all made from a 7:3 ratio of butyl acrylate to methyl methacrylate. Patch 17 has a 15 degree fiber angle, Patch 18 has a 5 degree fiber angle, and Patch 19 has a 25 degree fiber angle. Patches 9 and 10 were made from an 8:2 ratio of butyl acrylate and styrene, same as Patch 11. Patch 9 was an 80 mm long device, Patches 10 and 11 were 30 mm long devices. Device 3 was made from a 7:3 ratio of butyl acrylate to styrene.

Comparison of Fiber Angle within Patch

The angle of the fiber perpendicular to the length of the patch was varied in order to establish the mechanical properties for each orientation within the patch (FIGS. 19A-19C). The polyacrylate emulsion used for patch production was held constant as was the amount of emulsion applied post-fabrication. The patches were then cut in half then halved again to yield 4 pieces of patch for mechanical analysis as shown in FIGS. 26-29 and FIGS. 30A, 30B, 31A and 31B. The pieces of patch were provided in four different configurations: (a) transverse oriented fibers in dumbbells; (b) transverse oriented fibers in rectangular pieces; (c) laterally oriented fibers in dumbbell shape; and (d) laterally oriented fibers in rectangular shape. Dumbbell shape means that the patch segments are cut into a dumbbell pattern so that the center of the patch breaks where it is thinnest in order to accurately measure the tensile strength of the patches as is common practice in mechanical testing. Each piece of patch was tested under uniaxial mechanical load to extrapolate maximum force, tensile strength, and elastic modulus data for the patches.

Puncture Testing of Patches

Figure 32A:
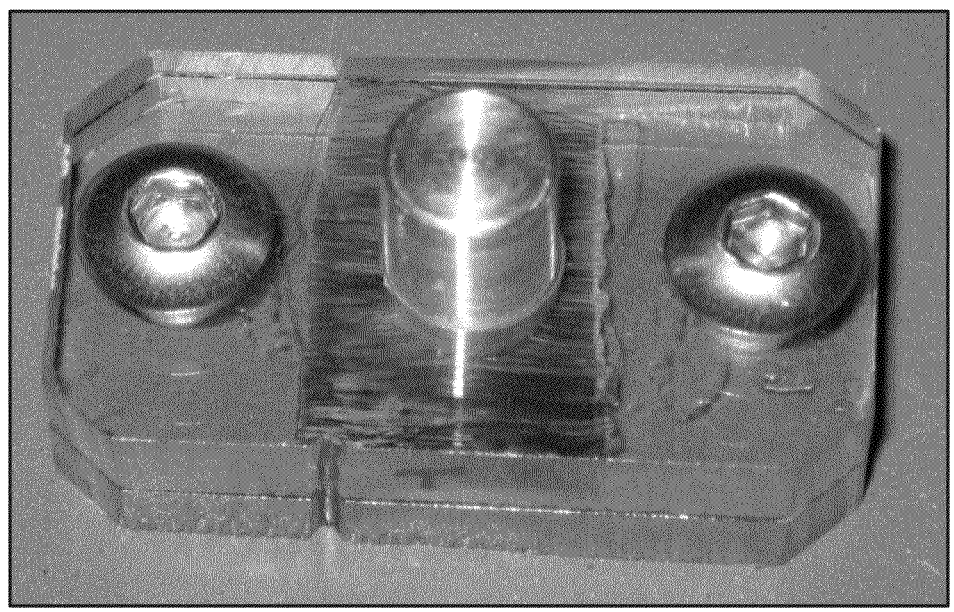
FIG. 32A is a digital photograph of a patch held in a punch test device according to embodiments of the present invention.
Figure 32B:
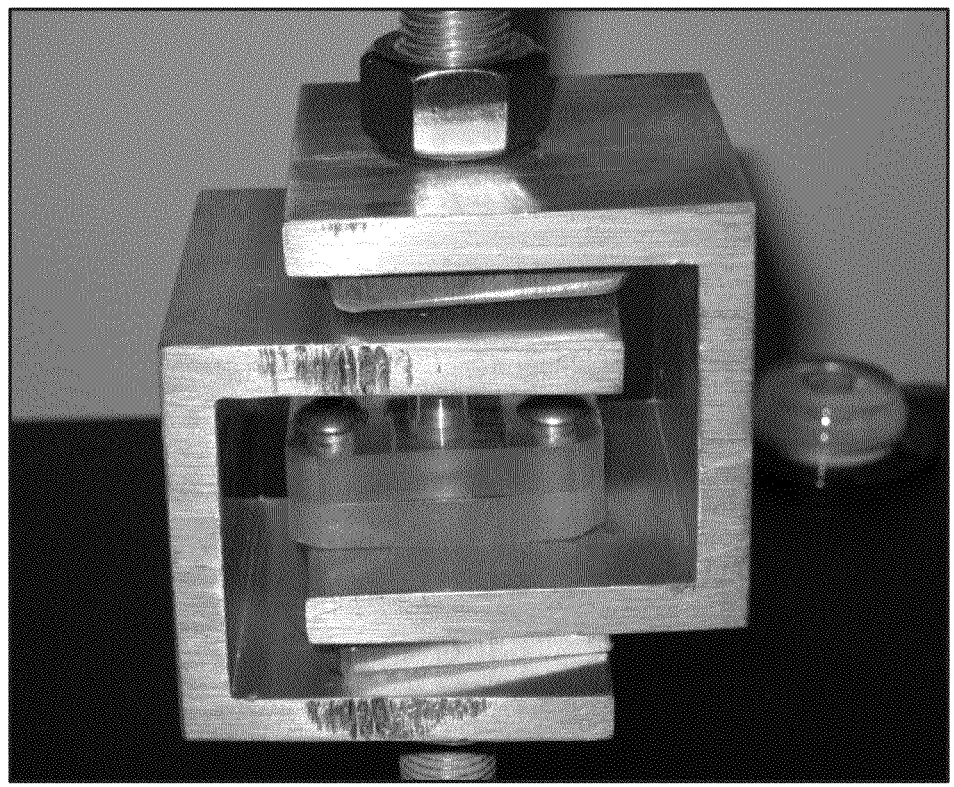
FIG. 32B is a digital photograph of the punch test device in a compression apparatus secured to a mechanical testing unit for shear strength evaluation of the patches according to embodiments of the present invention.
Figure 33A:
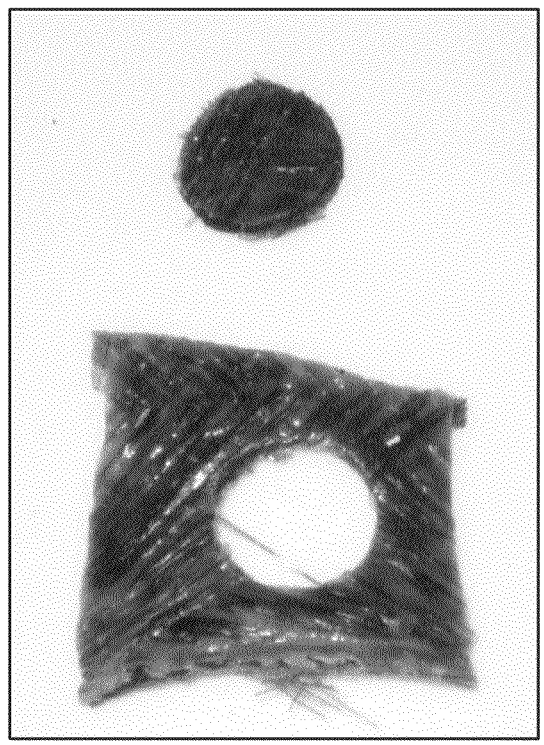
FIG. 33A is a digital photograph of a punched portion of the patch sample using the test set-up shown in FIGS. 32A and 32B.
Figure 33B:
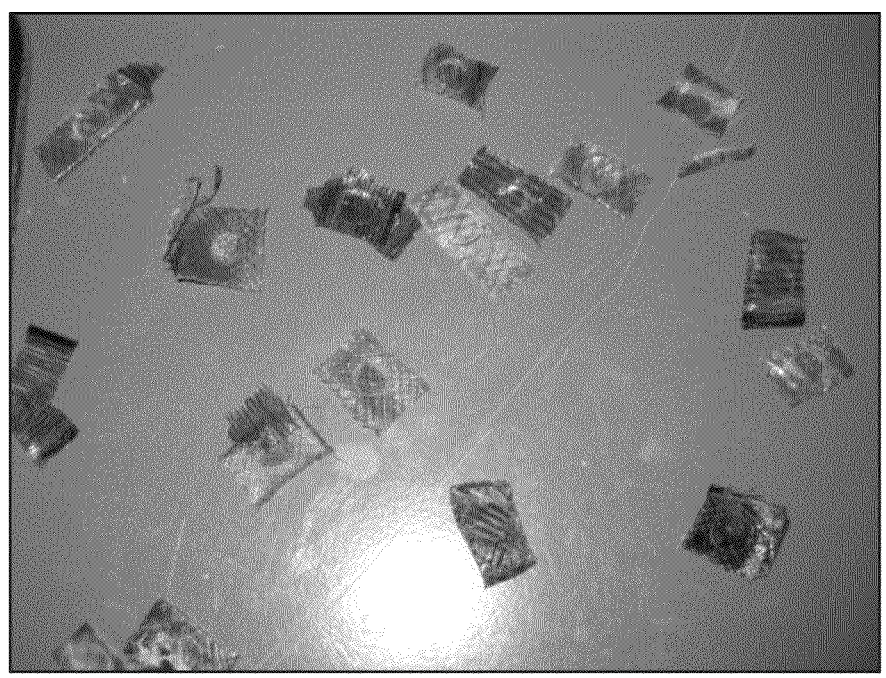
FIG. 33B is a digital photograph of various samples evaluated for shear strength according to embodiments of the present invention.
Figure 34A:
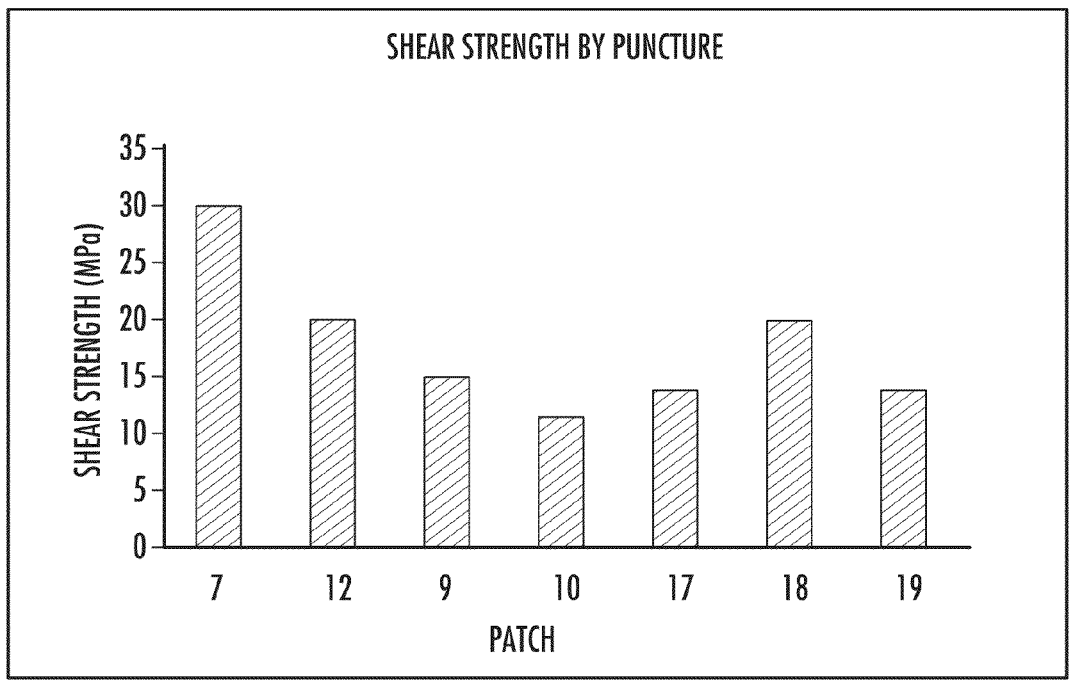
FIG. 34A is a bar graph of shear strength (MPa) by puncture versus patch number according to embodiments of the present invention.
Figure 34B:
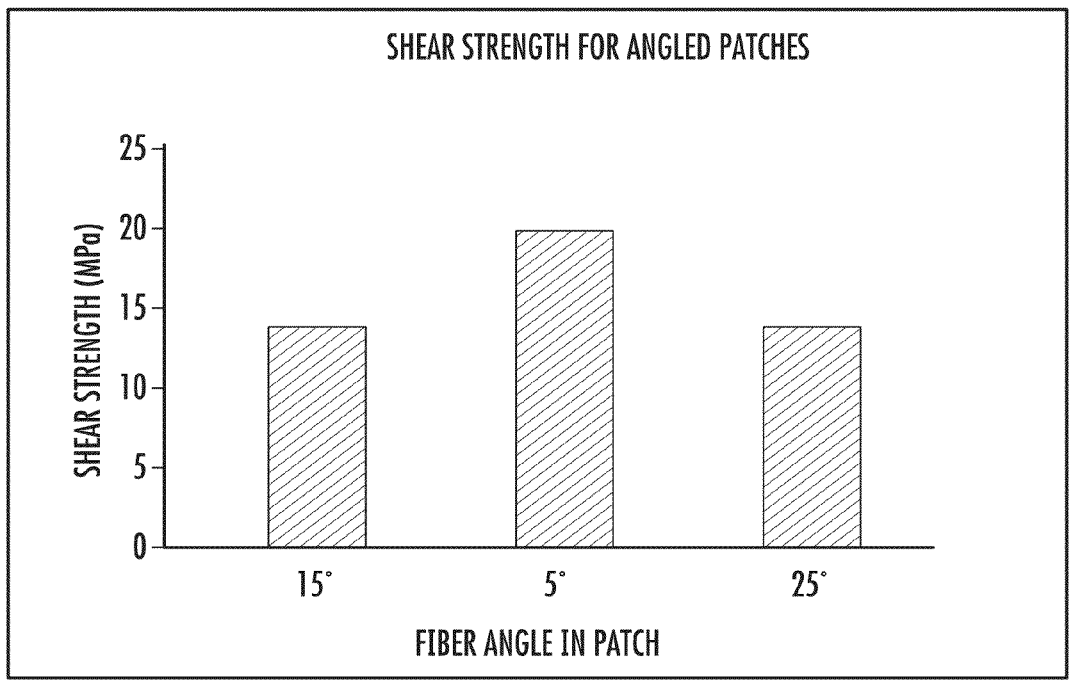
FIG. 34B is a bar graph of shear strength (MPa) versus fiber angle for angled patches according to embodiments of the present invention.

Shear strength of the patches was determine using a puncture testing where a 7.89 mm diameter punch was fabricated for testing as shown in FIG. 32A. The patch was secured between two pieces of polycarbonate using screws to hold in place, and a compression apparatus was secured to the mechanical testing unit for analysis as shown in FIG. 32B. Examples of patch samples evaluated using the punch testing system are shown in FIGS. 33A and 33B. FIG. 34A illustrates shear strength by patch number and FIG. 34B illustrates the shear strength by fiber angle in the patch (15 degrees, 5 degrees and 25 degrees).

Figure 35:
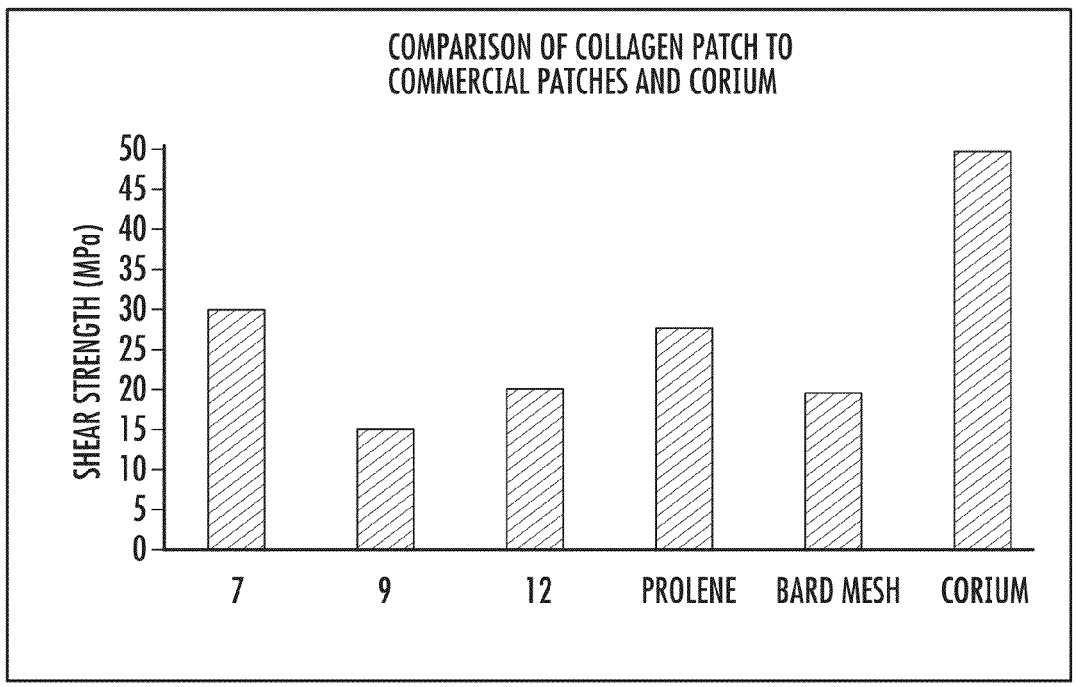
FIGS. 35 and 36 are bar graphs of shear strength (MPa) versus patch type or number comparing prototype data with samples of commercially available patches.
Figure 36:
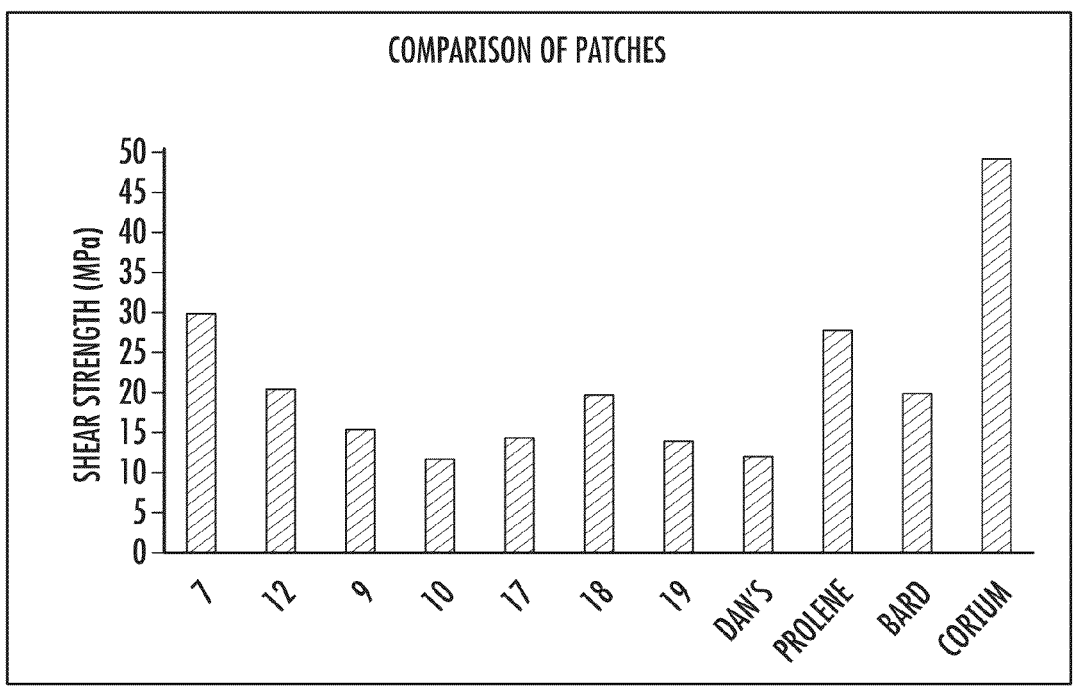

FIGS. 35 and 36 compare the shear strength of the different patches as well as commercial patches. The patches fabricated from 7 fiber strands (patch 7 and 12), displayed the highest shear strength, where patch 7 exhibited shear strength equal or higher than propylene synthetic patches. Single fiber patches had shear strengths within the 10-20 MPa range, where the 7 fiber patches were between 20-30 MPa. The propylene commercial patches (Prolene and Bard Meshes) had measured shear strengths between 20-30 MPa as well. Bovine corium was also tested for shear strength using the same puncture method, but a smaller diameter punch was needed due to the high strength of the specimens. The corium was observed having between 45 and 50 MPa.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. A medical device, comprising:
an elastic tube with a wall surrounding an axially extending cavity, the wall comprising a collagen fiber of a continuous length, said collagen fiber arranged to form a fiber mesh pattern of intersecting segments over at least a major length of the tube and said collagen fiber embedded in a non-cytotoxic polymeric film that extends over interstitial spaces defined by the fiber mesh pattern,
wherein the non-cytotoxic polymeric film comprises an acrylate, wherein said collagen fiber is derived from extruded soluble dermal collagen and the continuous length is in a range of 1 m to 100 m, wherein said collagen fiber is wound at an angle in a range of 1° to 90° relative to a first plane normal to a longitudinal axis of the tube, and wherein the tube includes multiple overlying layers of said collagen fiber to form the fiber mesh pattern of intersecting segments.

2. A medical device according to claim 1, wherein said collagen fiber has a diameter when dry in a range of 0.05 mm (average) to 0.2 mm (average), and wherein said collagen fiber is wound about the longitudinal axis of the tube at an angle in a range of 5° to 55° relative to the first plane normal to the longitudinal axis.

3. A medical device according to claim 1, wherein the tube is implantable in a hydrated state as artificial vascular material, and wherein the non-cytotoxic polymeric film cooperates with said collagen fiber to prevent fluid leakage through the tube.

4. A medical device according to claim 1, wherein said collagen fiber is a single collagen fiber or a single yarn of multiple collagen fibers in the multiple overlying layers, the single collagen fiber or single yarn having a diameter when dry in a range of 0.05 mm (average) to 0.2 mm (average).

5. A medical device according to claim 1, wherein the tube has reversible elasticity.

6. A medical device according to claim 1, wherein said collagen fiber is wound at an angle of 5° relative to the first plane normal to the longitudinal axis of the tube.

7. A medical device according to claim 1, wherein said collagen fiber is wound at an angle of 15° relative to the first plane normal to the longitudinal axis of the tube.

8. A medical device according to claim 1, wherein said collagen fiber is wound at an angle of 25° relative to the first plane normal to the longitudinal axis of the tube.

9. A medical patch comprising a continuous length collagen fiber, said continuous length collagen fiber arranged to form a fiber mesh pattern having a plurality of overlying layers defining interstitial spaces, wherein the patch comprises a polymeric film that extends over the interstitial spaces, and wherein the polymeric film comprises an acrylate.

10. A medical patch according to claim 9, wherein the patch is implantable.

11. A medical patch according to claim 9, wherein the patch is an external patch for a wound closure or treating a burn.

12. A medical patch according to claim 9, wherein the patch is a vascular graft or replacement device.

13. A medical patch according to claim 9, wherein the patch comprises a greater density of said continuous length collagen fiber on end portions thereof.

14. A medical patch according to claim 9, wherein said continuous length collagen fiber is cross-linked with NDGA.

15. A medical patch according to claim 9, wherein the patch has reversible elasticity.

16. A medical patch according to claim 9, wherein the polymeric film cooperates with said continuous length collagen fiber to prevent fluid leakage through the patch.

17. A medical patch according to claim 9, wherein said continuous length collagen fiber is provided as a multi-fiber yarn with a plurality of continuous length collagen fibers.

18. A medical patch according to claim 9, wherein said continuous length collagen fiber is arranged at an angle of 5° relative to a first plane normal to a longitudinal axis of the patch.

19. A medical patch according to claim 9, wherein said continuous length collagen fiber is arranged at an angle of 15° relative to a first plane normal to a longitudinal axis of the patch.

20. A medical patch according to claim 9, wherein said continuous length collagen fiber is arranged at an angle of 25° relative to a first plane normal to a longitudinal axis of the patch.

21. An artificial blood vessel, comprising:
a tube with a wall surrounding an axially extending cavity and comprising a wound collagen fiber of a continuous length arranged with a number of revolutions over at least a major length of the tube in a plurality of overlying stacked layers defining a fiber mesh pattern of intersecting segments with interstitial spaces, wherein the tube comprises a non-cytotoxic polymeric film, wherein the non-cytotoxic polymeric film is an acrylate film that extends across the interstitial spaces and over an external surface of said wound collagen fiber, wherein said collagen fiber is derived from extruded soluble dermal collagen and the continuous length is in a range of 1 m to 100 m, and wherein said collagen fiber forming the fiber mesh pattern of intersecting segments is wound at an angle or angles for each overlying layer in a range of 1° to 90° relative to a first plane normal to a longitudinal axis of the tube.

22. An artificial blood vessel according to claim 21, wherein the tube is elastic with sufficient rigidity to be able to elastically expand and contract in response to blood flow and pressure.

23. An artificial blood vessel according to claim 21, wherein said wound collagen fiber is cross-linked with NDGA.

24. An artificial blood vessel according to claim 21, wherein the non-cytotoxic polymeric film is an outer surface layer that extends across the interstitial spaces to define a closed external surface of the tube and includes at least one therapeutic agent.

25. An artificial blood vessel according to claim 21, wherein said wound collagen fiber is a single collagen fiber or a single yarn of multiple collagen fibers, each single collagen fiber or single yarn having a diameter in a range 0.05 mm (average, dry) to 0.2 mm (average, dry) and arranged in the plurality of overlying stacked layers, and wherein the tube has a length that is in a range of 1-8 cm.

26. An artificial blood vessel according to claim 21, wherein the tube has reversible elasticity.

27. An artificial blood vessel according to claim 21, wherein the non-cytotoxic polymeric film cooperates with said wound collagen fiber to prevent fluid leakage through the tube.

28. An artificial blood vessel according to claim 21, wherein said wound collagen fiber of a continuous length is wound at an angle of 5° relative to a first plane normal to a longitudinal axis of the tube.

29. An artificial blood vessel according to claim 21, wherein said wound collagen fiber of a continuous length is wound at an angle of 15° relative to a first plane normal to a longitudinal axis of the tube.

30. An artificial blood vessel according to claim 21, wherein said wound collagen fiber of a continuous length is wound at an angle of 25° relative to a first plane normal to a longitudinal axis of the tube.

31. An artificial blood vessel according to claim 21, wherein the acrylate film is formed from a liquid emulsion of butyl acrylate and styrene.

32. An artificial blood vessel according to claim 21, wherein the acrylate film is formed from a liquid emulsion of ethyl acrylate and methyl acrylate.

* * * * *

UNITED STATES PATENT AND TRADEMARK OFFICE
CERTIFICATE OF CORRECTION

PATENT NO. : 9,125,759 B2  
APPLICATION NO. : 13/729668  
DATED : September 8, 2015  
INVENTOR(S) : Greenhalgh et al.

Page 1 of 1

It is certified that error appears in the above-identified patent and that said Letters Patent is hereby corrected as shown below:

In the specification  
Column 11, Line 64: delete "10$e$" insert -- 10$c$ --

Column 13, Lines 37 and 38: delete "201" insert -- 20I --

Signed and Sealed this  
Fifteenth Day of March, 2016

Michelle K. Lee  
*Director of the United States Patent and Trademark Office*